(12) United States Patent
Pykett et al.

(10) Patent No.: US 7,192,769 B2
(45) Date of Patent: Mar. 20, 2007

(54) LYMPHOID TISSUE-SPECIFIC CELL PRODUCTION FROM HEMATOPOIETIC PROGENITOR CELLS IN THREE-DIMENSIONAL DEVICES

(75) Inventors: Mark J. Pykett, Boxford, MA (US); Michael Rosenzweig, Boston, MA (US); David T. Scadden, Weston, MA (US); Mark C. Poznansky, Charlestown, MA (US)

(73) Assignee: Cytomatrix, LLC, Chelmsford, MA (US)

( * ) Notice: Subject to any disclaimer, the term of this patent is extended or adjusted under 35 U.S.C. 154(b) by 499 days.

(21) Appl. No.: 10/161,097

(22) Filed: May 31, 2002

(65) Prior Publication Data

US 2003/0096404 A1    May 22, 2003

Related U.S. Application Data

(60) Division of application No. 09/574,749, filed on May 18, 2000, now Pat. No. 6,548,299, which is a continuation-in-part of application No. PCT/US99/26795, filed on Nov. 12, 1999.

(60) Provisional application No. 60/107,972, filed on Nov. 12, 1998.

(51) Int. Cl.
*C12N 5/06* (2006.01)

(52) U.S. Cl. ............... 435/373; 435/377; 435/382; 435/395; 435/399; 435/372.3

(58) Field of Classification Search ........... 435/373, 435/377, 382, 395, 399, 400, 372.3, 372.2, 435/372, 366; 623/16.11
See application file for complete search history.

(56) References Cited

U.S. PATENT DOCUMENTS

| | | | |
|---|---|---|---|
| 5,282,861 A | 2/1994 | Kaplan | |
| 5,443,950 A | 8/1995 | Naughton et al. | |
| 5,510,262 A | 4/1996 | Stephanopoulos | |
| 5,541,107 A | 7/1996 | Naughton et al. | |
| 5,580,781 A | 12/1996 | Naughton et al. | |
| 5,635,387 A | 6/1997 | Fei et al. | |
| 5,677,139 A | 10/1997 | Johnson et al. | |
| 6,440,734 B1 * | 8/2002 | Pykett et al. | ............ 435/372 |
| 6,548,299 B1 | 4/2003 | Pykett et al. | |
| 6,645,489 B2 | 11/2003 | Pykett et al. | |
| 2005/0079609 A1 | 4/2005 | Pykett et al. | |

FOREIGN PATENT DOCUMENTS

| | | |
|---|---|---|
| EP | 0 241 578 A | 10/1987 |
| EP | 0 358 506 | 3/1990 |
| EP | 0 560 279 A | 9/1993 |
| WO | WO 90/15877 A | 12/1990 |
| WO | WO 96/33265 | 10/1996 |
| WO | WO 97/33978 A | 9/1997 |
| WO | WO 99/15629 | 4/1999 |
| WO | WO 00/27999 | 5/2000 |
| WO | WO 01/11011 A2 | 2/2001 |
| WO | WO 01/21760 | 3/2001 |
| WO | WO 01/21766 | 3/2001 |
| WO | WO 03/100010 | 12/2003 |

OTHER PUBLICATIONS

Kim et al. J. Biomed. Materials Res. 1997; 35: 279-285.*
Vehof et al. Plast. Reconstr. Surg. 2001; 108: 434-443.*
Marshall et al. J. Hematother. Stem Cell Res. Oct. 2003; 12 (5): 565-574.*
Piascik et al. Exp. Hematol. Jun. 2001; 29(6): 766-774.*
Kuhn et al. Transplant. Proc. Aug. 2000; 32 (5): 1043-1044.*
McCarthy Lancet. Jul. 1, 2000; 356 (9233): 48.*
Banu et al. Cytokine. Mar. 21, 2001; 13 (6): 349-358.*
Rosenzweig, et al., "T-cell differentiation of human and non-human primate CD34+ hematopoietic progenitor cells using porcine thymic stroma", *Xenotransplantation*, 8, pp. 185-192 (2001).
Porter, et al., "A tissue of T cells", *Nature Biotechnology*, 18, pp. 714-715 (2000).
Poznansky, et al., "Efficient generation of human T cells from a tissue-engineered thymic organoid", *Nature Biotechnology*, 18, pp. 729-734 (2000).
Bagley, et al., "Extended culture of multipotent hematopoietic progenitors without cytokine augmentation in a novel three-dimensional device", *Experimental Hematology*, 27(3), pp. 496-504 (1999).
Bagley, et al., "Long-term three dimensional hematopoietic stem cell culture", *Amer. Chem. Soc.*, 126(Jan. 2003). ABSTRACT.
Bobyn, et al., "Characteristics of bone ingrowth and interface mechanics of a new porous tantalum biomaterial", *Journal of Bone & Joint Surgery (Br.)*, 81-B(5), pp. 907-914 (1999).

(Continued)

*Primary Examiner*—Stephen L. Rawlings
(74) *Attorney, Agent, or Firm*—Wolf, Greenfield & Sacks, P.C.

(57) ABSTRACT

The invention relates to a method for lymphoid tissue-specific cell production from hematopoietic progenitor cells in unique, three-dimensional culture devices, in the presence of antigen presenting cells and lymphoreticular stromal cells, and in the absence of exogenously added growth factors. The resulting lymphoid tissue-specific cells may be isolated at any sequential stage of differentiation and further expanded. The lymphoid tissue-specific cells also may be genetically altered at any stage of the process.

53 Claims, 2 Drawing Sheets

OTHER PUBLICATIONS

Clay, et al., "Potential use of T cell receptor genes to modify hematopoietic stem cells for the gene therapy of cancer", *Pathology Oncology Research*, 5(1), pp. 3-15 (1999).

Gardner, et al., "T-lymphopoietic capacity of cord blood-derived CD34+ progenitor cells", *Experimental Hematology*, 26, pp. 991-999 (1998).

Pawelec, et al., "Extrathymic T cell differentiation in vitro from human CD34+ stem cells", *Journal of Leukocyte Biology*, 64, pp. 733-739 (1998).

Rosenzweig, et al., "Enhanced maintenance and retroviral transduction of primitive hematopoietic progenitor cells using a novel three-dimensional culture system", *Gene Therapy*, 4(9), pp. 928-936 (1997).

Naughton, et al., "Three-dimensional bone marrow cell and tissue culture system", *Biotech. Adv.*, 15(2) (1997). ABSTRACT.

Freedman, et al., "Generation of human T lymphocytes from bone marrow CD34+ cells in vitro", *Nature Medicine*, 2(1), pp. 46-51 (1996).

Rosenzweig, et al., "In vitro T lymphopoiesis of human and rhesus CD34+ progenitor cells", *Blood*, 87(10), pp. 4040-4048 (1996).

Rosenzweig, et al., "In vitro T lymphopoiesis: A model system for stem cell gene therapy for AIDS", *Journal of Medical Primatology*, 25, pp. 192-200 (1996).

Wang, et al, "Multilineal hematopoiesis in a three-dimensional murine long-term bone marrow culture", *Experimental Hematology*, pp. 26-32, (1995).

Anderson, et al., "MHC class II-positive epithelium and mesenchyme cells are both required for T-cell development in the thymus", *Nature*, 362, pp. 70-73 (1993).

Boyd, et al. "The thymic microenvironment", *Immunology Today*, 14(9), pp. 445-459 (1993).

Van Ewijk, "T-cell differentiation is influenced by thymic microenvironments", *Annual Review of Immunology*, 9, pp. 591-615 (1991).

Naughton, et al., "Three-dimensional culture system for the growth of hematopoietic cells", *Prog. Clin.Biol. Res.*, 333, pp. 435-445, (1990).

Van Vliet, et al., "Stromal cell types in the developing thymus of the normal and nude mouse embryo", *European Journal of Immunology*, 15, pp. 675-681 (1985).

Naughton, G., et al., "Three-dimensional bone marrow cell and tissue culture system", *Biotechnology Advances*, vol. 15, No. 2, p. 401, 1997 (Abstract for U.S. Patent 5,541,107, listed above).

\* cited by examiner

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 1

Glu Ala Asp Pro Thr Gly His Ser Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 2

Ser Ala Tyr Gly Glu Pro Arg Lys Leu
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 3

Glu Val Asp Pro Ile Gly His Leu Tyr
  1               5

<210> SEQ ID NO 4
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 4

Phe Leu Trp Gly Pro Arg Ala Leu Val
  1               5

<210> SEQ ID NO 5
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 5

Met Glu Val Asp Pro Ile Gly His Leu Tyr
  1               5                   10

<210> SEQ ID NO 6
<211> LENGTH: 12
<212> TYPE: PRT
<213> ORGANISM: Artificial Sequence
<220> FEATURE:
<223> OTHER INFORMATION: Homo Sapiens source

<400> SEQUENCE: 6

Lys Ile Ser Gly Gly Pro Arg Ile Ser Tyr Pro Leu
  1               5                   10

<210> SEQ ID NO 7
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 7

Ala Leu Ser Arg Lys Val Ala Glu Leu
  1               5

<210> SEQ ID NO 8
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 8

Ala Ala Arg Ala Val Phe Leu Ala Leu
  1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Homo Sapiens source

<400> SEQUENCE: 9

Tyr Arg Pro Arg Pro Arg Arg Tyr
 1               5

<210> SEQ ID NO 10
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 10

Ser Pro Ser Ser Asn Arg Ile Arg Asn Thr
 1               5                  10

<210> SEQ ID NO 11
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 11

Val Leu Pro Asp Val Phe Ile Arg Cys
 1               5

<210> SEQ ID NO 12
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 12

Glu Glu Lys Leu Ile Val Val Leu Phe
 1               5

<210> SEQ ID NO 13
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 13

Glu Glu Lys Leu Ser Val Val Leu Phe
 1               5

<210> SEQ ID NO 14
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 14

Ala Cys Asp Pro His Ser Gly His Phe Val
 1               5                  10
```

```
<210> SEQ ID NO 15
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 15

Ala Arg Asp Pro His Ser Gly His Phe Val
 1               5                  10

<210> SEQ ID NO 16
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 16

Ser Tyr Leu Asp Ser Gly Ile His Phe
 1               5

<210> SEQ ID NO 17
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 17

Ser Tyr Leu Asp Ser Gly Ile His Ser
 1               5

<210> SEQ ID NO 18
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 18

Met Leu Leu Ala Val Leu Tyr Cys Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 19

Tyr Met Asn Gly Thr Met Ser Gln Val
 1               5

<210> SEQ ID NO 20
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 20

Tyr Met Asp Gly Thr Met Ser Gln Val
 1               5

<210> SEQ ID NO 21
```

```
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 21

Ala Phe Leu Pro Trp His Arg Leu Phe
 1               5

<210> SEQ ID NO 22
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 22

Ser Glu Ile Trp Arg Asp Ile Asp Phe
 1               5

<210> SEQ ID NO 23
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 23

Tyr Glu Ile Trp Arg Asp Ile Asp Phe
 1               5

<210> SEQ ID NO 24
<211> LENGTH: 15
<212> TYPE: PRT
<213> ORGANISM: Artificial Sequence
<220> FEATURE:
<223> OTHER INFORMATION: Homo Sapiens source

<400> SEQUENCE: 24

Gln Asn Ile Leu Leu Ser Asn Ala Pro Leu Gly Pro Gln Phe Pro
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Homo Sapiens source

<400> SEQUENCE: 25

Asp Tyr Ser Tyr Leu Gln Asp Ser Asp Pro Asp Ser Phe Gln Asp
 1               5                  10                  15

<210> SEQ ID NO 26
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 26

Ile Leu Thr Val Ile Leu Gly Val Leu
 1               5

<210> SEQ ID NO 27
<211> LENGTH: 9
```

```
<212> TYPE: PRT
<213> ORGANISM: Artificial Sequence
<220> FEATURE:
<223> OTHER INFORMATION: Homo Sapiens source

<400> SEQUENCE: 27

Lys Thr Trp Gly Gln Tyr Trp Gln Val
 1               5

<210> SEQ ID NO 28
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 28

Ile Thr Asp Gln Val Pro Phe Ser Val
 1               5

<210> SEQ ID NO 29
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 29

Tyr Leu Glu Pro Gly Pro Val Thr Ala
 1               5

<210> SEQ ID NO 30
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 30

Leu Leu Asp Gly Thr Ala Thr Leu Arg Leu
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Homo Sapiens source

<400> SEQUENCE: 31

Val Leu Tyr Arg Tyr Gly Ser Phe Ser Val
 1               5                  10

<210> SEQ ID NO 32
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 32

Leu Tyr Val Asp Ser Leu Phe Phe Leu
 1               5

<210> SEQ ID NO 33
<211> LENGTH: 11
<212> TYPE: PRT
```

```
<213> ORGANISM: Artificial Sequence
<220> FEATURE:
<223> OTHER INFORMATION: Homo Sapiens source

<400> SEQUENCE: 33

Ser Leu Leu Met Trp Ile Thr Gln Cys Phe Leu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 34

Ser Leu Leu Met Trp Ile Thr Gln Cys
1               5

<210> SEQ ID NO 35
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 35

Gln Leu Ser Leu Leu Met Trp Ile Thr
1               5

<210> SEQ ID NO 36
<211> LENGTH: 18
<212> TYPE: PRT
<213> ORGANISM: Artificial Sequence
<220> FEATURE:
<223> OTHER INFORMATION: Homo Sapiens source

<400> SEQUENCE: 36

His Leu Tyr Gln Gly Cys Gln Val Val Pro Leu Thr Ser Ile Ile Ser
1               5                   10                  15

Ala Val

<210> SEQ ID NO 37
<211> LENGTH: 9
<212> TYPE: PRT
<213> ORGANISM: Artificial Sequence
<220> FEATURE:
<223> OTHER INFORMATION: Homo Sapiens source

<400> SEQUENCE: 37

Leu Leu Gly Arg Asn Ser Phe Glu Val
1               5

<210> SEQ ID NO 38
<211> LENGTH: 15
<212> TYPE: PRT
<213> ORGANISM: Artificial Sequence
<220> FEATURE:
<223> OTHER INFORMATION: Rubella source

<400> SEQUENCE: 38

Trp Val Thr Pro Val Ile Gly Ser Gln Ala Arg Lys Cys Gly Leu
1               5                   10                  15

<210> SEQ ID NO 39
<211> LENGTH: 8
```

```
<212> TYPE: PRT
<213> ORGANISM: Artificial Sequence
<220> FEATURE:
<223> OTHER INFORMATION: Rubella source

<400> SEQUENCE: 39

Arg Val Ile Asp Pro Ala Ala Gln
 1               5

<210> SEQ ID NO 40
<211> LENGTH: 15
<212> TYPE: PRT
<213> ORGANISM: Artificial Sequence
<220> FEATURE:
<223> OTHER INFORMATION: Measles source

<400> SEQUENCE: 40

His Gln Ala Leu Val Ile Lys Leu Met Pro Asn Ile Thr Leu Leu
 1               5                  10                  15

<210> SEQ ID NO 41
<211> LENGTH: 9
<212> TYPE: PRT
<213> ORGANISM: Artificial Sequence
<220> FEATURE:
<223> OTHER INFORMATION: Papilloma source

<400> SEQUENCE: 41

Arg Leu Cys Val Gln Ser Thr His Val
 1               5

<210> SEQ ID NO 42
<211> LENGTH: 9
<212> TYPE: PRT
<213> ORGANISM: Artificial Sequence
<220> FEATURE:
<223> OTHER INFORMATION: Papilloma source

<400> SEQUENCE: 42

Tyr Val Arg Asp Gly Asn Pro Tyr Ala
 1               5

<210> SEQ ID NO 43
<211> LENGTH: 10
<212> TYPE: PRT
<213> ORGANISM: Artificial Sequence
<220> FEATURE:
<223> OTHER INFORMATION: Papilloma source

<400> SEQUENCE: 43

Gly Tyr Asn Lys Pro Leu Cys Asp Leu Leu
 1               5                  10

<210> SEQ ID NO 44
<211> LENGTH: 12
<212> TYPE: PRT
<213> ORGANISM: Artificial Sequence
<220> FEATURE:
<223> OTHER INFORMATION: Influenza source

<400> SEQUENCE: 44

Lys Gly Ile Leu Gly Phe Val Phe Thr Leu Thr Val
 1               5                  10

<210> SEQ ID NO 45
<211> LENGTH: 13
<212> TYPE: PRT
```

-continued

```
<213> ORGANISM: Artificial Sequence
<220> FEATURE:
<223> OTHER INFORMATION: Influenza source

<400> SEQUENCE: 45

Glu Lys Tyr Val Lys Gln Asn Thr Leu Lys Leu Ala Thr
 1               5                   10

<210> SEQ ID NO 46
<211> LENGTH: 9
<212> TYPE: PRT
<213> ORGANISM: Artificial Sequence
<220> FEATURE:
<223> OTHER INFORMATION: Hepatitis B source

<400> SEQUENCE: 46

Trp Leu Ser Leu Leu Val Pro Phe Val
 1               5

<210> SEQ ID NO 47
<211> LENGTH: 9
<212> TYPE: PRT
<213> ORGANISM: Artificial Sequence
<220> FEATURE:
<223> OTHER INFORMATION: Hepatitis B source

<400> SEQUENCE: 47

Phe Leu Gly Gly Thr Thr Val Cys Leu
 1               5

<210> SEQ ID NO 48
<211> LENGTH: 9
<212> TYPE: PRT
<213> ORGANISM: Artificial Sequence
<220> FEATURE:
<223> OTHER INFORMATION: Hepatitis C source

<400> SEQUENCE: 48

Tyr Leu Val Ala Tyr Gln Ala Thr Val
 1               5

<210> SEQ ID NO 49
<211> LENGTH: 9
<212> TYPE: PRT
<213> ORGANISM: Artificial Sequence
<220> FEATURE:
<223> OTHER INFORMATION: Hepatitis C source

<400> SEQUENCE: 49

Gly Leu Arg Asp Leu Ala Val Ala Val
 1               5

<210> SEQ ID NO 50
<211> LENGTH: 14
<212> TYPE: PRT
<213> ORGANISM: Artificial Sequence
<220> FEATURE:
<223> OTHER INFORMATION: Hepatitis C source

<400> SEQUENCE: 50

Gly Tyr Lys Val Leu Val Leu Asn Pro Ser Val Ala Ala Thr
 1               5                   10

<210> SEQ ID NO 51
<211> LENGTH: 10
<212> TYPE: PRT
<213> ORGANISM: Artificial Sequence
```

```
<220> FEATURE:
<223> OTHER INFORMATION: Hepatitis C source

<400> SEQUENCE: 51

Lys Leu Val Ala Leu Gly Ile Asn Ala Val
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Tetanus source

<400> SEQUENCE: 52

Gln Tyr Ile Lys Ala Asn Ser Lys Phe Ile Gly Ile Tyr Gln Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Homo Sapiens source

<400> SEQUENCE: 53

Thr Tyr Glu Leu Ala Pro Val Phe Val Leu Leu Glu Tyr Val Thr
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Homo Sapiens source

<400> SEQUENCE: 54

Leu Lys Lys Met Arg Phe Ile Ile Gly Trp Pro Gly Gly Ser Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Homo Sapiens source

<400> SEQUENCE: 55

Lys Lys Gly Ala Ala Ala Ile Gly Ile Gly Thr Asp Ser Val Ile
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Homo Sapiens source

<400> SEQUENCE: 56

Pro Leu Cys Ser Ala Leu Leu Val Arg Glu Glu Gly Leu Met
1               5                   10

<210> SEQ ID NO 57
<211> LENGTH: 15
<212> TYPE: PRT
<213> ORGANISM: Artificial Sequence
<220> FEATURE:
```

-continued

```
<223> OTHER INFORMATION: Homo Sapiens source

<400> SEQUENCE: 57

Trp Leu Met Trp Arg Ala Lys Gly Thr Thr Gly Phe Glu Ala His
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Homo Sapiens source

<400> SEQUENCE: 58

Val Ile Val Met Leu Thr Pro Leu Val Glu Asp Gly Val Lys Gln Cys
1               5                   10                  15
```

US 7,192,769 B2

LYMPHOID TISSUE-SPECIFIC CELL PRODUCTION FROM HEMATOPOIETIC PROGENITOR CELLS IN THREE-DIMENSIONAL DEVICES

RELATED APPLICATIONS

This application is a divisional of application Ser. No. 09/574,749 filed on May 18, 2000 now U.S. Pat. No. 6,548,299, entitled LYMPHOID TISSUE-SPECIFIC CELL PRODUCTION FROM HEMATOPOIETIC PROGENITOR CELLS IN THREE-DIMENSIONAL DEVICES, which in turn is a continuation-in-part of PCT/US99/26795 application filed on Nov. 12, 1999, which in turn claims priority from U.S. Provisional application Ser. No. 60/107,972 filed on Nov. 12, 1998. The contents of the foregoing applications are hereby expressly incorporated by reference.

FIELD OF THE INVENTION

The invention pertains to the co-culture of hematopoietic progenitor cells and lymphoreticular stromal cells in three-dimensional devices, resulting in unexpectedly high numbers of lymphoid tissue-specific cell progeny.

BACKGROUND OF THE INVENTION

A characteristic of the immune system is the specific recognition of antigens. This includes the ability to discriminate between self and non-self antigens and a memory-like potential that enables a fast and specific reaction to previously encountered antigens. The vertebrate immune system reacts to foreign antigens with a cascade of molecular and cellular events that ultimately results in the humoral and cell-mediated immune response.

The major pathway of the immune defense involving antigen-specific recognition commences with the trapping of the antigen by antigen presenting cells (APCs), such as dendritic cells or macrophages, and the subsequent migration of these cells to lymphoid organs (e.g., thymus). There, the APCs present antigen to subclasses of T cells classified as mature T helper cells. Upon specific recognition of the presented antigen, the mature T helper cells can be triggered to become activated T helper cells. The activated T helper cells regulate both the humoral immune response by inducing the differentiation of mature B cells to antibody producing plasma cells and the cell-mediated immune response by activation of mature cytotoxic T cells.

The thymus has been shown to be an obligatory factor in T cell differentiation of hematopoietic cells. Based upon the murine model, it is believed that the presence of a three dimensional organ is required, as in vitro models that do not include the thymus and a three dimensional structure fail to support T cell lymphopoiesis (Owen J J, et al., Br Med Bull., 1989, 45:350–360). The process of differentiation, however, appears to begin prior to progenitor cells contacting the thymus.

Primitive hematopoictic progenitors in the fetal liver or bone marrow give rise to lineage committed cells, including progenitors committed to the T lymphoid lineage. These most immature cells are identified by the surface expression of CD34. T cell lineage committed cells express CD34, but no discrete expression of other epitopes found only on T cell progenitors has been described. Further, T lymphocyte differentiation normally occurs via a series of discrete developmental stages. Primitive progenitor cells which do not express lymphocyte specific cell surface markers (CD34+ CD3− CD4− CD8−) migrate to the thymus where they acquire, through a series of maturational events, the phenotype CD34− CD3− CD4+ CD8−. These cells then mature into double positive CD4+ CD8+ cells, most of which are CD3+, although CD3 expression is not universally detectable. These cells further undergo both positive and negative selection, and mature to develop into single positive T cells (CD4+ CD8− or CD4− CD8+). These cells ultimately migrate into the peripheral circulation as naive T cells.

T cell disorders and diseases represent major health problems. Recent progress has been made using gene therapy to treat conditions involving T lymphocytes, including AIDS. This has fostered increased interest in the development of laboratory techniques that allow in vitro evaluations of potential genetic therapies for these conditions.

The understanding of T cell differentiation has been hampered by the limited availability of technologies which permit in vitro T cell differentiation. To date, T cell differentiation studies have been largely confined to the SCID-hu mouse in vivo model. In vitro technologies have been based on thymic explant studies and primate thymic monolayers. In a recent advance, primate thymic stroma cultures have been shown to provide an expedient, although inefficient, system for examining T cell development, enabling in vitro T cell differentiation in a reproducible manner. However, the purity and number of T cells generated this way, as well as the relatively short half-life of the cultures, generally results in limited applicability to more advanced studies of T cell differentiation and function.

SUMMARY OF THE INVENTION

The invention, in one important part, involves improved methods for culturing hematopoietic progenitor cells that direct their development toward lymphoid tissue-specific lineages without the addition of exogenous growth factors. Thus, one aspect of the invention is the culture of hematopoietic progenitor cells to generate progeny committed to a specific lineage. Another aspect is an improvement in the rate and the number of differentiated progeny that can be obtained from a sample of hematopoietic progenitor cells.

We describe herein a system that takes advantage of biocompatible, open-pore, three-dimensional matrices, and uses human and non-human lymphoreticular stromal cells to provide the appropriate conditions for the expansion and differentiation of human and non-human hematopoietic progenitor cells toward a specific cell lineage. T lymphocytes, for example, derived from these cultures respond normally to a variety of stimuli and express the diversity of markers expected of mature T cells.

This system provides significant advantages over existing techniques. For example, it can provide for the rapid generation of a large number of differentiated progeny necessary for laboratory analysis and/or therapeutic uses, including for in vitro testing of potential gene therapy strategies or for reinfusion into subjects in vivo. The matrix itself can be implanted into subjects for in vivo studies of hematopoietic cell growth. The system also can reasonably replicate the complex process of hematopoietic cell maintenance, expansion and/or differentiation toward a specific lineage.

Surprisingly, according to the invention, it has been discovered that hematopoietic progenitor cells co-cultured with lymphoreticular stromal cells in a porous solid scaffold, without the addition of exogenous growth agents, generate at a fast rate an unexpectedly high number of functional, differentiated progeny of a lymphoid-specific lineage. The lymphoid tissue from which lymphoreticular stromal cells are derived helps determine the lineage-commitment hematopoietic progenitor cells undertake, resulting in the lineage-specificity of the differentiated progeny. Also surprising, according to the invention, is the discovery that lesser amounts of nonlymphoid cells (i.e. myelo-monocytic cells) are generated from the co-culture of hematopoietic progenitor cells and lymphoreticular stromal cells in a porous solid scaffold of the invention when compared to existing methodology. Thus, the present invention permits for the rapid generation of a large number of differentiated, lymphoid-specific cells from a relatively small number of hematopoietic progenitor cells. Such results were never before realized using known art methodologies (e.g., as in U.S. Pat. No. 5,677,139 by Johnson et al., which describes the in vitro differentiation of $CD3^+$ cells on primate thymic stroma monolayers, or as in U.S. Pat. No. 5,541,107 by Naughton et al., which describes a three-dimensional bone marrow cell and tissue culture system).

According to one aspect of the invention, a method for in vitro production of lymphoid tissue-specific cells is provided. The method involves introducing an amount of hematopoietic progenitor cells and an amount of lymphoreticular stromal cells into a porous, solid matrix having interconnected pores of a pore size sufficient to permit the hematopoietic progenitor cells and the lymphoreticular stromal cells to grow throughout the matrix. The hematopoietic progenitor cells and the lymphoreticular stromal cells are then co-cultured. The amount of the lymphoreticular stromal cells utilized is sufficient to support the growth and differentiation of the hematopoietic progenitor cells. In one embodiment, co-culturing occurs under conditions sufficient to produce at least a 10-fold increase in the number of lymphoid tissue origin cells. In preferred embodiments, co-culturing occurs under conditions sufficient to produce at least a 20, 50, 100, 200, 300 or 400-fold increase in the number of lymphoid tissue origin cells. In some embodiments, after the co-culturing, harvesting of the lymphoid tissue origin cells may be performed.

In certain embodiments, the hematopoietic progenitor cells may be pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage.

The hematopoietic progenitor cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the lymphoreticular stromal cells may be also derived from at least one of the foregoing lymphoid soft tissues. In important embodiments, the lymphoreticular stromal cells are thymic stromal cells and the multipotent progenitor cells and/or committed progenitor cells are committed to a T cell lineage. In further important embodiments, the lymphoreticular stromal cells are skin-derived stromal cells and the multipotent progenitor cells and/or committed progenitor cells are committed to a T cell lineage. In other embodiments, the hematopoietic progenitor cells and/or the lymphoreticular stromal cells may be genetically altered.

In certain embodiments, the hematopoietic progenitor cells and the lymphoreticular stromal cells are autologous (e.g., originate from the same individual). In important embodiments, the method further comprises antigen presenting cells. In some embodiments, the hematopoietic progenitor cells, the lymphoreticular stromal cells, and the antigen presenting cells are all autologous. In one embodiment, the method further comprises antigen presenting cells non-autologous to the hematopoietic progenitor cells and the lymphoreticular stromal cells.

In some embodiments, the hematopoietic progenitor cells and the lymphoreticular stromal cells are non-autologous (e.g., allogeneic, syngeneic and/or xenogeneic in origin). In important embodiments, the method further comprises antigen presenting cells. Various embodiments are provided wherein different source combinations for each of the cells in the co-culture are encompassed by the present invention. For example, the hematopoietic progenitor cells, the lymphoreticular stromal cells, and the antigen presenting cells can be autologous, or non-autologous and each one from a different source. In another instance, the hematopoietic progenitor cells and the antigen presenting cells can be autologous or non-autologous. In still another instance, the lymphoreticular stromal cells and the antigen presenting cells are non-autologous.

In certain embodiments, antigen presenting cells may be added to the co-culture of hematopoietic progenitor cells and lymphoreticular stromal cells. Various embodiments are provided encompassing different source combinations for each of the cells in the co-culture, and wherein the lymphoid tissue-specific cells produced are to be used in transplantation into a host. For example, each of the hematopoietic progenitor cells, lymphoreticular stromal cells and/or antigen presenting cells may be autologous or non-autologous to the cells of the host.

In any of the foregoing aspects and embodiments of the invention at least one antigen may be included, or added after, the co-culture of the cells. In any of the foregoing embodiments involving antigen presenting cells, it is preferred that the antigen presenting cells are mature.

According to any of the foregoing aspects and embodiments, the method of the invention can include hematopoietic progenitor cells, lymphoreticular stromal cells and/or antigen presenting cells that are genetically altered.

In one important embodiment of the invention, the hematopoietic progenitor cells are of human origin and the lymphoreticular stromal cells are also of human origin. Antigen presenting cells can also be of human and non-human origin. In another embodiment, the hematopoietic progenitor cells are of human origin and the lymphoreticular stromal cells are of non-human origin. In preferred embodiments, non-human lymphoreticular stromal cells are of murine origin.

In certain embodiments, the lymphoreticular stromal cells are seeded to the matrix at the same time as the hematopoietic progenitor cells. In other embodiments, the lymphoreticular stromal cells are seeded to the matrix prior to inoculating the hematopoietic progenitor cells.

The porous matrix can be one that is an open cell porous matrix having a percent open space of at least 50%, and preferably at least 75%. In one embodiment the porous solid matrix has pores defined by interconnecting ligaments having a diameter at midpoint, on average, of less than 150 µm. Preferably the porous solid matrix is a metal-coated reticulated open cell foam of carbon containing material, the metal coating being selected from the group consisting of tantalum, titanium, platinum (including other metals of the platinum group), niobium, hafnium, tungsten, and combinations thereof. In preferred embodiments, whether the porous solid matrix is metal-coated or not, the matrix is coated with a biological agent selected from the group consisting of collagens, fibronectins, laminins, integrins, angiogenic factors, anti-inflammatory factors, glycosaminoglycans, vitrogen, antibodies and fragments thereof, functional equivalents of these factors (including fragments thereof), and combinations thereof. Most preferably the metal coating is tantalum coated with a biological agent. In certain other embodiments, the porous solid matrix having seeded hematopoietic progenitor cells and their progeny, and lymphoreticular stromal cells (and/or antigen presenting cells), is impregnated with a gelatinous agent that occupies pores of the matrix.

The preferred embodiments of the invention are solid, unitary macrostructures, i.e. not beads or packed beads. They also involve nonbiodegradable materials.

According to any of the foregoing embodiments, the method of the invention can include culturing the cells in an environment that is free of hematopoietic progenitor cell survival and proliferation factors such as interleukins 3, 6 and 11. Still another embodiment of the invention is performing the co-culturing of the hematopoietic progenitor cells and the lymphoreticular stromal cells in an environment that is free altogether of stromal cell conditioned medium and exogenously added hematopoietic growth factors that promote hematopoietic cell maintenance, expansion and/or differentiation, other than serum.

As will be understood, according to the invention, it is possible now to co-culture hematopoietic progenitor cells and lymphoreticular stromal cells (that may or may not include antigen presenting cells), in an environment that is free of exogenously added hematopoietic growth factors that promote hematopoietic cell maintenance, expansion and/or differentiation for as little as 7 days and to obtain large numbers of differentiated progeny of a specific lineage.

According to any of the foregoing embodiments, the method of the invention can include co-culturing of the hematopoietic progenitor cells, the lymphoreticular stromal cells, and/or the antigen presenting cells with an exogenously added agent selected from the group consisting of stromal cell conditioned medium, and a hematopoietic growth factor that promotes hematopoietic cell maintenance, expansion and/or differentiation, and influences cell localization. In certain embodiments, the hematopoietic growth factor that promotes hematopoietic cell maintenance, expansion and/or differentiation, and influences cell localization, may be an agent that includes interleukin 3, interleukin 6, interleukin 7, interleukin 11, interleukin 12, stem cell factor, FLK-2 ligand, FLT-2 ligand, Epo, Tpo, GMCSF, GCSF, Oncostatin M, and MCSF.

According to another aspect of the invention, a method for in vivo maintenance, expansion and/or differentiation of hematopoietic progenitor cells is provided. The method involves implanting into a subject a porous, solid matrix having seeded therein hematopoietic progenitor cells (which may include their progeny) and lymphoreticular stromal cells. The porous matrix has interconnected pores of a pore size sufficient to permit the cells to grow throughout the matrix and is an open cell porous matrix having a percent open space of at least 50%, and preferably at least 75%. Various embodiments are provided, wherein the porous solid matrix has one or more of the preferred characteristics as described above.

In certain embodiments, hematopoietic progenitor cells (that may include progeny) and lymphoreticular stromal cells are attached to the matrix by introducing in vitro an amount of hematopoietic progenitor cells and an amount of lymphoreticular stromal cells into the porous solid matrix, and co-culturing the hematopoietic progenitor cells in an environment that is free of stromal cell conditioned medium and free of exogenously added hematopoietic growth factors that promote hematopoietic cell maintenance, expansion and/or differentiation, other than serum. Various other embodiments are provided, wherein the co-culturing is performed under conditions as described above. In yet other embodiments, the porous solid matrix having seeded hematopoietic progenitor cells (that may include progeny) and lymphoreticular stromal cells is impregnated with a gelatinous agent that occupies pores of the matrix.

According to one aspect of the invention, a method for inducing T cell tolerance, is provided. The method involves producing lymphoid tissue-specific cells according to any of the foregoing co-culture methods of the invention that involve the co-culture of cells that include non-autologous cells, under conditions sufficient to induce the formation of T cells and/or T cell progenitors and to inhibit immune activation of the formed cells.

According to yet another aspect of the invention, a method for treating a subject to enhance immune tolerance in the subject, is provided. The method involves administering to a subject in need of such treatment an amount of lymphoid tissue-specific cells produced according to any of the foregoing co-culture methods of the invention that involve the co-culture of cells that may include non-autologous cells, wherein the amount of lymphoid tissue-specific cells is sufficient to enhance in the subject immune tolerance to an autologous or a non-autologous antigen. Various embodiments are provided wherein preferred cell types and porous matrix are as described elsewhere herein (see, e.g., below).

According to still another aspect of the invention, a method for inducing T cell reactivity, is provided. The method involves producing lymphoid tissue-specific cells according to any of the foregoing co-culture methods of the invention that involve the co-culture of cells that may include autologous and/or non-autologous cells, in the presence of at least one antigen, under conditions sufficient to induce formation of T cells or T cell progenitors having specificity for the at least one antigen. In important embodiments, the at least one antigen is added to the co-culture in a further step after formation of T cells or T cell progenitors.

In certain embodiments, the hematopoietic progenitor cells may be pluripotent stem cells, multipotent progenitor cells and/or progenitor cells committed to specific hematopoietic lineages. The hematopoietic progenitor cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and/or Peyer's patches. In other embodiments, the lymphoreticular stromal cells may be also derived from at least one of the foregoing lymphoid soft tissues. In preferred embodiments, the lymphoreticular stromal cells are thymic stromal cells and the multipotent progenitor cells and/or committed progenitor cells are committed to a T cell lineage. In other embodiments, the hematopoietic progenitor cells and/or the lymphoreticular stromal cells may be genetically altered.

In important embodiments, antigen presenting cells may be added to the co-culture. Antigen presenting cells include cells such as dendritic cells, monocytes/macrophages, Langerhans cells, Kupfer cells, microglia, alveolar macrophages and B cells. In other embodiments, the antigen presenting cells are derived from hematopoietic progenitor cells in vitro. Various embodiments are provided, wherein the hematopoietic progenitor cells, the lymphoreticular stromal cells, and the porous solid matrix have one or more of the preferred characteristics as described above, and the cells are cultured as described above. The antigen presenting cells may be derived from hematopoietic progenitor cells in vitro. In important embodiments the antigen presenting cells are mature. In further embodiments, the method further comprises administering a co-stimulatory agent to the co-culture. Preferred co-stimulatory agents include lymphocyte function associated antigen 3 (LFA-3), CD2, CD40, CD80/B7-1, CD86/B7-2, OX-2, CD70, and CD82.

In yet another aspect of the invention, a solid porous matrix is provided wherein hematopoietic progenitor cells, with or without their progeny, and lymphoreticular stromal cells are attached to the solid porous matrix. The lymphoreticular stromal cells are present in an amount sufficient to support the growth and differentiation of hematopoietic progenitor cells. In certain embodiments, the hematopoietic progenitor cells are attached to the lymphoreticular stromal cells. In further embodiments, the solid porous matrix may include antigen presenting cells (progeny and/or nonprogeny). Preferably the antigen presenting cells are mature. In yet further embodiments, the porous matrix further comprises at least one antigen. The porous matrix can be one that is an open cell porous matrix having a percent open space of at least 50%, and preferably at least 75%. In one embodiment the porous solid matrix has pores defined by interconnecting ligaments having a diameter at midpoint, on average, of less than 150 µm. Preferably the porous solid matrix is a metal-coated reticulated open cell foam of carbon containing material, the metal coating being selected from the group consisting of tantalum, titanium, platinum (including other metals of the platinum group), niobium, hafnium, tungsten, and combinations thereof. In preferred embodiments, whether the porous solid matrix is metal-coated or not, the matrix is coated with a biological agent selected from the group consisting of collagens, fibronectins, laminins, integrins, angiogenic factors, anti-inflammatory factors, glycosaminoglycans, vitrogen, antibodies and fragments thereof, functional equivalents of these factors, and combinations thereof. Most preferably the metal coating is tantalum coated with a biological agent. In certain other embodiments the porous solid matrix having seeded hematopoietic progenitor cells and lymphoreticular stromal cells, is impregnated with a gelatinous agent that occupies pores of the matrix.

In a further aspect of the invention, a method for identifying an agent suspected of affecting hematopoietic cell development, is provided. The method involves introducing an amount of hematopoietic progenitor cells and an amount of lymphoreticular stromal cells into a porous, solid matrix having interconnected pores of a pore size sufficient to permit the hematopoietic progenitor cells and the lymphoreticular stromal cells to grow throughout the matrix, co-culturing the hematopoietic progenitor cells and the lymphoreticular stromal cells in the presence of at least one candidate agent suspected of affecting hematopoietic cell development (in a test co-culture), and determining whether the at least one candidate agent affects hematopoietic cell development in the test co-culture by comparing the test co-culture hematopoietic cell development to a control co-culture, whereby hematopoietic progenitor cells and lymphoreticular stromal cells are co-cultured in the absence of the at least one candidate agent. Various embodiments are provided, wherein the hematopoietic progenitor cells, the lymphoreticular stromal cells, and the porous solid matrix have one or more of the preferred characteristics as described above, and the cells are cultured as described above. In certain embodiments, hematopoietic progenitor cell development includes hematopoietic progenitor cell maintenance, expansion, differentiation toward a specific cell lineage, and/or cell-death (including apoptosis). In preferred embodiments the lymphoreticular stromal cells are thymic stromal cells.

In another aspect of the invention, a method for isolating from a cell culture an agent suspected of affecting hematopoietic cell development, is provided. The method involves introducing an amount of hematopoietic progenitor cells and an amount of lymphoreticular stromal cells into a porous, solid matrix having interconnected pores of a pore size sufficient to permit the hematopoietic progenitor cells and the lymphoreticular stromal cells to grow throughout the matrix, co-culturing the hematopoietic progenitor cells and the lymphoreticular stromal cells, obtaining a test-supernatant from the co-culture, comparing the test-supernatant to a control-supernatant, and obtaining a subfraction of the test-supernatant that contains an agent suspected of affecting hematopoietic cell development that is absent from the control-supernatant. In certain embodiments the agent suspected of affecting hematopoietic cell development may be present in the control-supernatant and absent from the test-supernatant. In other embodiments, the agent suspected of affecting hematopoietic cell development in one supernatant may be different to an agent suspected of affecting hematopoietic cell development in the other supernatant (e.g., in size, via a post-translational modification, in an alternatively spliced variant form, etc.). Various embodiments are provided, wherein the hematopoietic progenitor cells, the lymphoreticular stromal cells, and the porous solid matrix have one or more of the preferred characteristics as described above, and the cells are cultured as described above. In certain embodiments, hematopoietic progenitor cell development includes hematopoietic progenitor cell maintenance, expansion, differentiation toward a specific cell lineage, and/or cell-death (including apoptosis). In preferred embodiments, the lymphoreticular stromal cells are thymic stromal cells. In certain other embodiments, the control culture system of the prior art (where the control-supernatant can be obtained from) is the one described in U.S. Pat. No. 5,677,139 by Johnson et al.

These and other aspects of the invention, as well as various advantages and utilities, will be more apparent with reference to the detailed description of the preferred embodiments.

DETAILED DESCRIPTION OF THE INVENTION

Figure 1A:
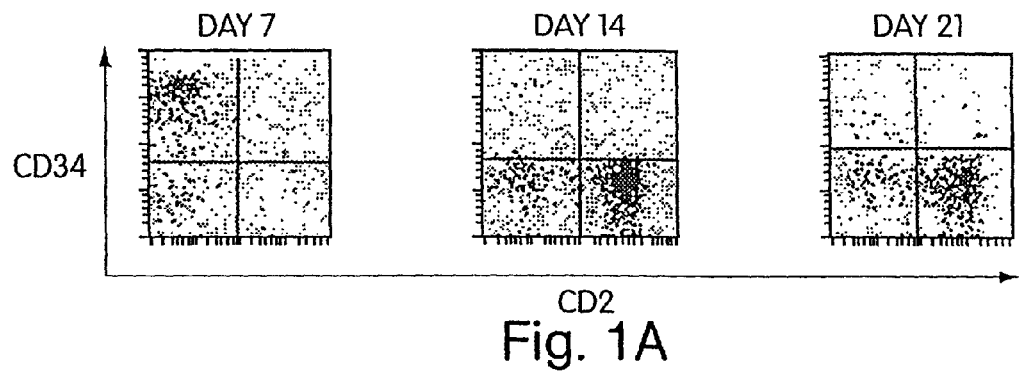
FIG. 1 shows the differentiation of human $CD34^+$ progenitor cells into T cells, in co-culture with murine thymic stroma cells on a three-dimensional matrix; the data in FIG. 1($a$) is shows the acquisition of CD2 and the down-regulation of the hematopoietic progenitor cell marker CD34; the data in FIG. 1($b$) shows the discrete populations of SP $CD4^+$ and SP $CD8^+$ cells, including their DP $CD4^+CD8^+$ precursors; the data in FIGS. 1($c$ and $d$) shows that all $CD4^+$($c$) and $CD8^+$($d$) cells co-expressed CD3.
Figure 1B:
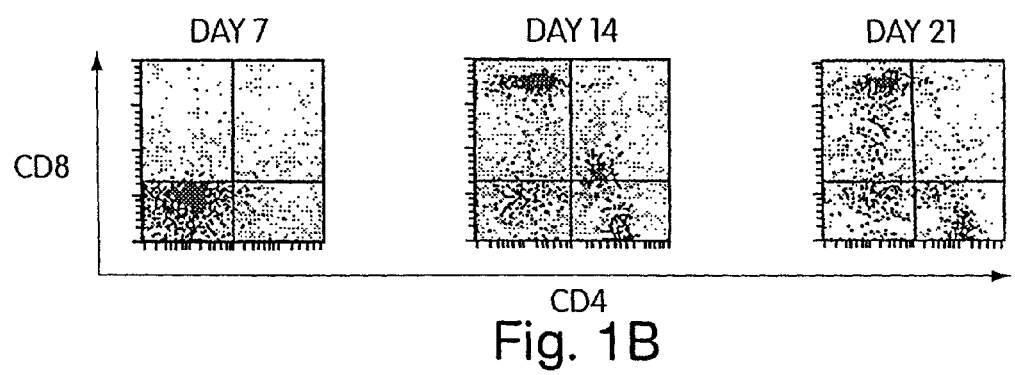
Figure 1C:
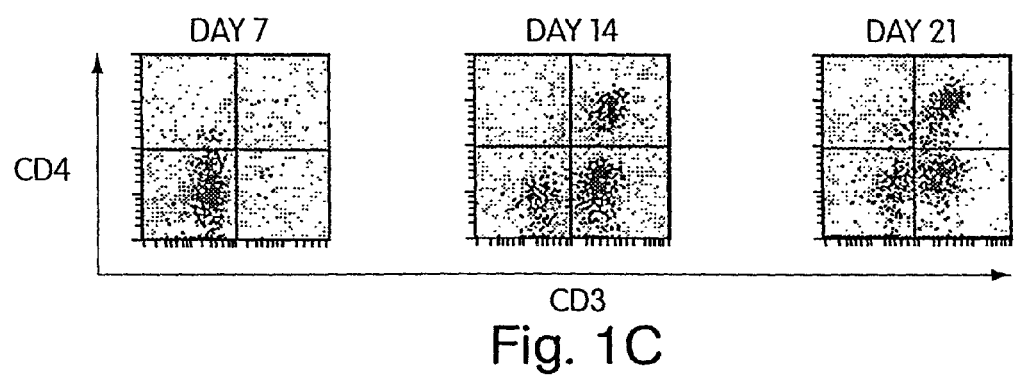
Figure 1D:
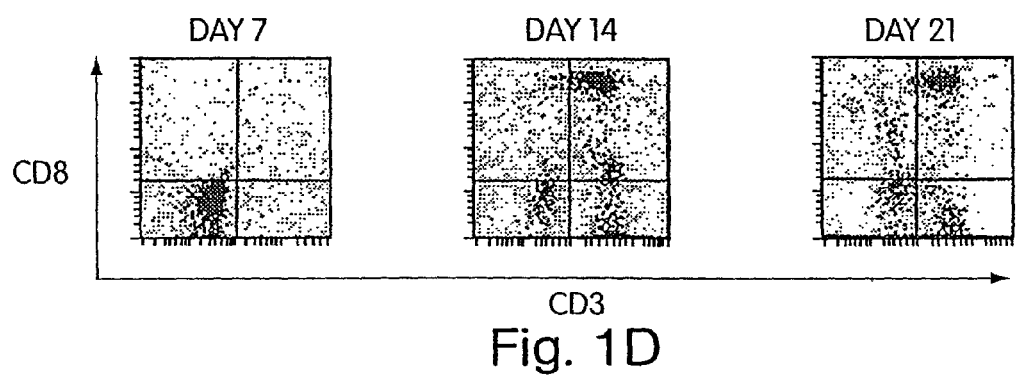

The invention involves the unexpected discovery that hematopoietic progenitor cells co-cultured with lymphoreticular stromal cells in a porous solid scaffold, without the addition of exogenous growth agents, generate at a fast rate an unexpectedly high number of functional, differentiated progeny of a lymphoid tissue-specific lineage. Also surprising, according to the invention, has been the discovery that lesser amounts of nonlymphoid cells (i.e. myelo-monocytic cells) are generated from the co-culture of hematopoietic progenitor cells and lymphoreticular stromal cells in a porous solid scaffold of the invention when compared to existing technology. Thus, the present invention, and in contrast to what has been previously achieved in the art, permits for the rapid generation of a large number of differentiated, lymphoid-specific cells from a relatively small number of hematopoietic progenitor cells.

Methods of the invention are therefore useful inter alia for establishing immunocompetence in patients suffering from an immunodeficiency, e.g., a T cell or B cell deficiency, e.g., a thymic based immunodeficiency, e.g., a congenital immunodeficiency due to thymic aplasia or dysfunction, an acquired immune disorder, e.g., AIDS, immunoincompetence resulting form a neoplastic disease, or immunoincompetence resulting from a medical procedure, e.g., chemotherapy, immunocompetence in response to an antigen, etc. Methods of generating immune cells in vitro and/or or ex vivo that could be used in transplantation, implantation, autoimmune diseases, and/or infectious diseases are also contemplated.

The invention in one aspect involves culturing hematopoietic cells in a porous solid matrix, in the absence of exogenous growth agents, to produce lymphoid tissue origin (lymphoid tissue-specific) cells.

A porous, solid matrix, is defined as a three-dimensional structure with "sponge-like" continuous pores forming an interconnecting network. The matrix can be rigid or elastic, and it provides a scaffold upon which cells can grow throughout. Its pores are interconnected and provide the continuous network of channels extending through the matrix and also permit the flow of nutrients throughout. A preferred matrix is an open cell foam matrix having a percent open space of at least 50% and preferably 75%. Thus, it is preferred that the open space comprise the majority of the matrix. This is believed to maximize cell migration, cell-cell contact, space for cell growth and accessibility to nutrients. It is preferred that the porous matrix be formed of a reticulated matrix of ligaments which at their center point are less than 150 μm in diameter, preferably 60 μm, whereby a cell can reside on or interact with a portion of the ligament. Preferably, the average pore diameter is on the order of 300 μm, which resembles cancellous bone. Suitable matrices can be obtained using a number of different methods. Examples of such methods include solvent casting or extraction of polymers, track etching of a variety of materials, foaming of a polymer, the replamineform process for hydroxyapatite, and other methodologies well known to those of ordinary skill in the art. The materials employed can be natural or synthetic, including biological materials such as proteins, hyaluronic acids, synthetic polymers such as polyvinyl pyrolidones, polymethylmethacrylate, methyl cellulose, polystyrene, polypropylene, polyurethane, ceramics such as tricalcium phosphate, calcium aluminate, calcium hydroxyapatite and ceramic-reinforced or coated polymers. If the starting material for the scaffold is not metal, a metal coating can be applied to the three-dimensional matrix. Metal coatings provide further structural support and/or cell growth and adhesive properties to the matrix. Preferred metals used as coatings comprise tantalum, titanium, platinum and metals in the same element group as platinum, niobium, hafnium, tungsten, and combinations of alloys thereof. Coating methods for metals include a process such as CVD (Chemical Vapor Deposition).

The preferred matrix, refered to herein throughout as Cellfoam (Cytomatrix, Woburn, Mass.), is described in detail in U.S. Pat. No. 5,282,861, and is incorporated herein by reference. More specifically, the preferred matrix is a reticulated open cell substrate formed by a lightweight, substantially rigid foam of carbon-containing material having open spaces defined by an interconnecting network, wherein said foam material has interconnected continuous channels, and a thin film of metallic material deposited onto the reticulated open cell substrate and covering substantially all of the interconnecting network to form a composite porous biocompatible material creating a porous microstructure similar to that of natural cancellous bone.

Additionally, such matrices can be coated with biological agents which can promote cell adhesion for the cultured hematopoietic progenitor cells, allowing for improved migration, growth and proliferation. Moreover, when these matrices are used for the in vivo maintenance, expansion and/or differentiation of hematopoietic progenitor cells (i.e., when the matrices with the cells are implanted into a subject, -see also discussion below), biological agents that promote angiogenesis (vascularization) and biological agents that prevent/reduce inflammation may also be used for coating of the matrices. Preferred biological agents comprise collagens, fibronectins, laminins, integrins, angiogenic factors, anti-inflammatory factors, glycosaminoglycans, vitrogen, antibodies and fragments thereof, functional equivalents of these agents, and combinations thereof.

Angiogenic factors include platelet derived growth factor (PDGF), vascular endothelial growth factor (VEGF), basic fibroblast growth factor (bFGF), bFGF-2, leptins, plasminogen activators (tPA, uPA), angiopoietins, lipoprotein A, transforming growth factor-β, bradykinin, angiogenic oligosaccharides (e.g., hyaluronan, heparan sulphate), thrombospondin, hepatocyte growth factor (also known as scatter factor) and members of the CXC chemokine receptor family. Anti-inflammatory factors comprise steroidal and non-steroidal compounds and examples include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

In certain embodiments of the invention the porous solid matrix having seeded hematopoietic progenitor cells, with or without their progeny, and lymphoreticular stromal cells is impregnated with a gelatinous agent that occupies pores of the matrix. The hematopoietic progenitor cells, with or without their progeny, and/or the lymphoreticular stromal cells can be seeded prior to, substantially at the same time as, or following impregnation (or infiltration) with a gelatinous agent. For example, the cells may be mixed with the agent and seeded at the same time as the the impregnation of the matrix with the agent. In some embodiments, the cells are seeded onto the porous solid matrix prior to application of the agent. In certain embodiments the lymphoreticular stromal cells are seeded in a similar manner. A person of ordinary skill in the art can easily determine seeding conditions. Preferably the lymphoreticular stromal cells are seeded prior to the hematopoietic progenitor cells and prior to impregnation with the agent.

"Impregnation" with a gelatinous agent can serve, inter alia, to contain the cells within the matrix, or to help maintain and/or enhance cell attachment onto the matrix. The "gelatinous" agent may be one that can be maintained in a fluid state initially (i.e. gelable), and after its application into the matrix, be gelatinized in situ in the matrix. Such gelatinization may occur in a number of different ways, including altering the agent's temperature, irradiating the agent with an energy source (e.g., light), etc. The "gelatinous" agent also is characterized by its ability to allow the nutrients of the growth media to reach the cells throughout the matrix. Exemplary "gelatinous" agents include cellulosic polysaccharides (such as cellulose, hemicellulose, methylcellulose, and the like), agar, agarose, albumin, algal mucin, mucin, mucilage, collagens, glycosaminoglycans, and proteoglycans (including their sulphated forms). In certain embodiments, the gelatinous agent may impregnate the matrix completely, in some embodiments partially, and in other embodiments minimally, serving only as a coating of all or some of the outer surfaces of the matrix. In important embodiments where gelatinous agents are employed, the "gelatinous" agent is methylcellulose and the impregnation is complete.

According to the invention, hematopoietic progenitor cells and lymphoreticular stromal cells are co-cultured in one of the foregoing porous solid matrices, in the absence of exogenous growth agents, to produce lymphoid tissue origin (lymphoid tissue-specific) cells.

"Lymphoid tissue origin" (lymphoid tissue-specific) cells, as used herein, refer to cells that may be produced in vitro or in vivo according to the invention, and are substantially similar (e.g., in properties and function) to the cells produced naturally in vivo from organs and tissues that include the bone marrow, thymus, lymph nodes, spleen and mucosal associated lymphoid tissue (unencapsulated tissue lining the respiratory, alimentary and genito-urinary tracts).

"Hematopoietic progenitor cells" as used herein refers to immature blood cells having the capacity to self-renew and to differentiate into the more mature blood cells (also described herein as "progeny") comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). It is known in the art that such cells may or may not include $CD34^+$ cells. $CD34^+$ cells are immature cells present in the "blood products" described below, express the CD34 cell surface marker, and are believed to include a subpopulation of cells with the "progenitor cell" properties defined above. It is well known in the art that hematopoietic progenitor cells include pluripotent stem cells, multipotent progenitor cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage.

The hematopoietic progenitor cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for $CD34^+$ cells. As mentioned earlier, $CD34^+$ cells are thought in is the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

The cells co-cultured with the hematopoietic progenitor cells according to the methods of the invention are lymphoreticular stromal cells. "Lymphoreticular stromal cells" as used herein may include, but are not limited to, all cell types present in a lymphoid tissue which are not lymphocytes or lymphocyte precursors or progenitors, e.g., epithelial cells, endothelial cells, mesothelial cells, dendritic cells, splenocytes and macrophages. Lymphoreticular stromal cells also include cells that would not ordinarily function as lymphoreticular stromal cells, such as fibroblasts, which have been genetically altered to secrete or express on their cell surface the factors necessary for the maintenance, growth and/or differentiation of hematopoietic progenitor cells, including their progeny. Lymphoreticular stromal cells are derived from the disaggregation of a piece of lymphoid tissue (see discussion below and the Examples). Such cells according to the invention are capable of supporting in vitro the maintenance, growth and/or differentiation of hematopoietic progenitor cells, including their progeny. By "lymphoid tissue" it is meant to include bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. "Lymphoid soft tissue" as used herein includes, but is not limited to, tissues such as thymus, spleen, liver, lymph node, skin, tonsil, adenoids and Peyer's patch, and combinations thereof.

Lymphoreticular stromal cells provide the supporting microenvironment in the intact lymphoid tissue for the maintenance, growth and/or differentiation of hematopoietic progenitor cells, including their progeny. The microenvironment includes soluble and cell surface factors expressed by the various cell types which comprise the lymphoreticular stroma. Generally, the support which the lymphoreticular stromal cells provide may be characterized as both contact-dependent and non-contact-dependent.

Lymphoreticular stromal cells may be autologous ("self") or non-autologous ("non-self," e.g., allogeneic, syngeneic or xenogeneic) with respect to hematopoietic progenitor cells or antigen presenting cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. Lymphoreticular stroma cells may be obtained from the lymphoid tissue of a human or a non-human subject at any time after the organ/tissue has developed to a stage (i.e., the maturation stage) at which it can support the maintenance growth and/or differentiation of hematopoietic progenitor cells. The stage will vary between organs/tissues and between subjects. In primates, for example, the maturation stage of thymic development is achieved during the second trimester. At this stage of development the thymus can produce peptide hormones such as thymulin, $\alpha_1$ and $\beta_4$-thymosin, and thymopoietin, as well as other factors required to provide the proper microenvironment for T cell differentiation. The different maturation stages for the different organs/tissues and between different subjects are well known in the art.

The lymphoid tissue from which lymphoreticular stromal cells are derived usually determines the lineage-commitment hematopoietic progenitor cells undertake, resulting in the lineage-specificity of the differentiated progeny. In certain embodiments, the lymphoreticular stromal cells are thymic stromal cells and the multipotent progenitor cells and/or committed progenitor cells are committed to a T cell lineage. In other embodiments, the lymphoreticular stromal cells may be splenic stromal cells and the multipotent progenitor cells and/or committed progenitor cells are committed to a B cell lineage. Also surprising, according to the invention, has been the discovery that the highest yield of differentiated progeny occurs when human hematopoietic progenitor cells are cultured in the presence of xenogeneic (non-human) lymphoreticular stromal cells. Preferably the xenogeneic lymphoreticular stromal cells are of murine origin.

Unexpectedly, it has also been discovered that lesser amounts of nonlymphoid-specific cells (i.e. myelo-monocytic cells) are generated from the foregoing co-cultures when compared to existing methodology. In other words, more homogeneous differentiation of cells with fewer contaminant cell types (nonlymphoid) is observed form cultures of the present invention on Cellfoam, enabling the preservation of immature progenitors ($CD34^+$ cells) while promoting the differentiation of more mature T progeny.

Various other embodiments are provided, wherein the lymphoreticular stromal cells may be genetically altered. The lymphoreticular stromal cells may be transfected with exogenous DNA that encodes, for example, one of the hematopoietic growth factors described above (see fibroblast discussion above).

As mentioned earlier, lymphoreticular stromal cells are derived from the disaggregation of a piece of lymphoid tissue, forming cell suspensions. Preferably, single cell suspensions are generated. These lymphoreticular stromal cell suspensions may be used directly, or made non-mitotic by procedures standard in the tissue culture art. Examples of such methods are irradiation of lymphoreticular stromal cells with a gamma-ray source or incubation of the cells with mitomycin C for a sufficient amount of time to render the cells mitotically inactive. Mitotic inactivation is preferred when the lymphoreticular stromal cells are of human origin (to eliminate progenitor cells that may be present in the suspension). The lymphoreticular stromal cells may then be seeded into a three-dimensional matrix of the invention and permitted to attach to a surface of the porous, solid matrix. It should be noted that the lymphoreticular stromal cells may alternatively be cryopreserved for later use or for storage and shipment to remote locations, such as for use in connection with the sale of kits. Cryopreservation of cells cultured in vitro is well established in the art. Subsequent to isolation (and/or mitotic inactivation) of a cell sample, cells may be cryopreserved by first suspending the cells in a cryopreservation medium and then gradually freezing the cell suspension. Frozen cells are typically stored in liquid nitrogen or at an equivalent temperature in a medium containing serum and a cryopreservative such as dimethyl sulfoxide.

The co-culture of the hematopoietic progenitor cells (and progeny thereof) with lymphoreticular stromal cells, preferably occurs under conditions sufficient to produce a percent increase in the number of lymphoid tissue origin cells deriving from the hematopoietic progenitor cells. The conditions used refer to a combination of conditions known in the art (e.g., temperature, $CO_2$ and $O_2$ content, nutritive media, time-length, etc.). The time sufficient to increase the number of cells is a time that can be easily determined by a person skilled in the art, and can vary depending upon the original number of cells seeded. The amounts of hematopoietic progenitor cells and lymphoreticular stromal cells initially introduced (and subsequently seeded) into the porous solid matrix may vary according to the needs of the experiment. The ideal amounts can be easily determined by a person skilled in the art in accordance with needs. Preferably, the lymphoreticular stromal cells would form a confluent layer onto the matrix. Hematopoietic progenitor cells may be added at different numbers. As an example, discoloration of the media over a certain period of time can be used as an indicator of confluency. Additionally, and more precisely, different numbers of hematopoietic progenitor cells or volumes of the blood product can be cultured under identical conditions, and cells can be harvested and counted over regular time intervals, thus generating the "control curves". These "control curves" can be used to estimate cell numbers in subsequent occasions (see the Examples section).

The conditions for determining colony forming potential are similarly determined. Colony forming potential is the ability of a cell to form progeny. Assays for this are well known to those of ordinary skill in the art and include seeding cells into a semi-solid matrix, treating them with growth factors, and counting the number of colonies.

In preferred embodiments of the invention, the hematopoietic progenitor cells may be harvested. "Harvesting" hematopoietic progenitor cells is defined as the dislodging or separation of cells from the matrix. This can be accomplished using a number of methods, such as enzymatic and non-enzymatic, centrifugal, electrical or by size, or the one preferred in the present invention, by flushing of the cells using the media in which the cells are incubated. The cells can be further collected, separated, and further expanded generating even larger populations of differentiated progeny.

As mentioned above, the hematopoietic progenitor cells, and progeny thereof, can be genetically altered. Genetic alteration of a hematopoietic progenitor cell includes all transient and stable changes of the cellular genetic material which are created by the addition of exogenous genetic material. Examples of genetic alterations include any gene therapy procedure, such as introduction of a functional gene to replace a mutated or nonexpressed gene, introduction of a vector that encodes a dominant negative gene product, introduction of a vector engineered to express a ribozyme and introduction of a gene that encodes a therapeutic gene product. Natural genetic changes such as the spontaneous rearrangement of a T cell receptor gene without the introduction of any agents are not included in this concept. Exogenous genetic material includes nucleic acids or oligonucleotides, either natural or synthetic, that are introduced into the hematopoietic progenitor cells. The exogenous genetic material may be a copy of that which is naturally present in the cells, or it may not be naturally found in the cells. It typically is at least a portion of a naturally occurring gene which has been placed under operable control of a promoter in a vector construct.

The invention involves the unexpected discovery that hematopoietic progenitor cells can be more efficiently genetically altered if the genetic alteration occurs while the hematopoietic progenitor cells are on and within a solid porous matrix as described above.

Various techniques may be employed for introducing nucleic acids into cells. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

In the present invention, the preferred method of introducing exogenous genetic material into hematopoietic cells is by transducing the cells in situ on the matrix using replication-deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells, and specific utility for use in the method of the present invention. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome. Despite these apparent limitations, delivery of a therapeutically effective amount of a therapeutic agent via a retrovirus can be efficacious if the efficiency of transduction is high and/or the number of target cells available for transduction is high.

Yet another viral candidate useful as an expression vector for transformation of hematopoietic cells is the adenovirus, a double-stranded DNA virus. Like the retrovirus, the adenovirus genome is adaptable for use as an expression vector for gene transduction, i.e., by removing the genetic information that controls production of the virus itself. Because the adenovirus functions usually in an extrachromosomal fashion, the recombinant adenovirus does not have the theoretical problem of insertional mutagenesis. On the other hand, adenoviral transformation of a target hematopoietic cell may not result in stable transduction. However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable vectors are available for transferring exogenous genetic material into hematopoietic cells. The selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation. The promoter characteristically has a specific nucleotide sequence necessary to initiate transcription. Optionally, the exogenous genetic material further includes additional sequences (i.e., enhancers) required to obtain the desired gene transcription activity.

For the purpose of this discussion an "enhancer" is simply any nontranslated DNA sequence which works contiguous with the coding sequence (in cis) to change the basal transcription level dictated by the promoter. Preferably, the exogenous genetic material is introduced into the hematopoietic cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfinann et al., *Proc. Natl. Acad. Sci. USA* 88:4626–4630 (1991)), adenosine deaminase, phosphoglycerol kinase (PGK), pyruvate kinase, phosphoglycerol mutase, the actin promoter (Lai et al., *Proc. Natl. Acad. Sci. USA* 86: 10006–10010 (1989)), and other constitutive promoters known to those of skill in the art. In addition, many viral promoters function constitutively in eukaryotic cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified hematopoietic cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector preferably includes a selection gene, for example, a neomycin resistance gene, for facilitating selection of hematopoietic cells that have been transfected or transduced with the expression vector. Alternatively, the hematopoietic cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The selection and optimization of a particular expression vector for expressing a specific gene product in an isolated hematopoietic cell is accomplished by obtaining the gene, preferably with one or more appropriate control regions (e.g., promoter, insertion sequence); preparing a vector construct comprising the vector into which is inserted the gene; transfecting or transducing cultured hematopoietic cells in vitro with the vector construct; and determining whether the gene product is present in the cultured cells.

TABLE 1

| Human Gene Therapy Protocols Approved by RAC: 1990–1994 | | |
|---|---|---|
| Severe combined immune deficiency (SCID) due to ADA deficiency | Autologous lymphocytes transduced with human ADA gene | Jul. 31, 1990 |
| Advanced cancer | Tumor-infiltrating lymphocytes transduced with tumor necrosis factor gene | Jul. 31, 1990 |
| Advanced cancer | Immunization with autologous cancer cells transduced with tumor necrosis factor gene | Oct. 7, 1991 |
| Advanced cancer | Immunization with autologous cancer cells transduced with interleukin-2 gene | Oct. 7, 1991 |
| Asymptomatic patients infected with HIV-1 | Murine Retro viral vector encoding HIV-1 genes [HIV-IT(V)] | Jun. 7, 1993 |
| AIDS | Effects of a transdominant form of rev gene on AIDS intervention | Jun. 7, 1993 |
| Advanced cancer | Human multiple-drug resistance (MDR) gene transfer | Jun. 8, 1993 |
| HIV infection | Autologous lymphocytes transduced with catalytic ribozyme that cleaves HIV-1 RNA (Phase I study) | Sep. 10, 1993 |
| Metastatic melanoma | Genetically engineered autologous tumor vaccines producing interleukin-2 | Sep. 10, 1993 |
| HIV infection | Murine Retro viral vector encoding HIV-IT(V) genes (open label Phase I/II trial) | Dec. 3, 1993 |
| HIV infection (identical twins) | Adoptive transfer of syngeneic cytotoxic T lymphocytes (Phase I/II pilot study) | Mar. 3, 1994 |
| Breast cancer (chemo-protection during therapy) | Use of modified Retro virus to introduce chemotherapy resistance sequences into normal hematopoietic cells (pilot study) | Jun. 9, 1994 |

TABLE 1-continued

Human Gene Therapy Protocols Approved by RAC: 1990–1994

| | | |
|---|---|---|
| Fanconi's anemia | Retro viral mediated gene transfer of the Fanconi anemia complementation group C gene to hematopoietic progenitors | Jun. 9, 1994 |
| Metastatic prostate carcinoma | Autologous human granulocyte macrophage-colony stimulating factor gene transduced prostate cancer vaccine *(first protocol to be approved under the accelerated review process; ORDA = Office of Recombinate DNA Activities) | ORDA/NIH Aug. 3, 1994* |
| Metastatic breast cancer | In vivo infection with breast-targeted Retro viral vector expressing antisense c-fox or antisense c-myc RNA | Sep. 12, 1994 |
| Metastatic breast cancer (refractory or recurrent) | Non-viral system (liposome-based) for delivering human interleukin-2 gene into autologous tumor cells (pilot study) | Sep. 12, 1994 |
| Mild Hunter syndrome | Retro viral-mediated transfer of the iduronate-2-sulfatase gene into lymphocytes | Sep. 13, 1994 |
| Advanced mesothelioma | Use of recombinant adenovirus (Phase I study) | Sep. 13, 1994 |

The foregoing (Table 1), represent only examples of genes that can be delivered according to the methods of the invention. Suitable promoters, enhancers, vectors, etc., for such genes are published in the literature associated with the foregoing trials. In general, useful genes replace or supplement function, including genes encoding missing enzymes such as adenosine deaminase (ADA) which has been used in clinical trials to treat ADA deficiency and cofactors such as insulin and coagulation factor VIII. Genes which affect regulation can also be administered, alone or in combination with a gene supplementing or replacing a specific function. For example, a gene encoding a protein which suppresses expression of a particular protein-encoding gene can be administered. The invention is particularly useful in delivering genes which stimulate the immune response, including genes encoding viral antigens, tumor antigens, cytokines (e.g. tumor necrosis factor) and inducers of cytokines (e.g. endotoxin).

Employing the culture conditions described in greater detail below, it is possible according to the invention to preserve hematopoietic progenitor cells and to stimulate the expansion of hematopoietic progenitor cell number and/or colony forming unit potential. Once expanded, the cells, for example, can be returned to the body to supplement, replenish, etc. a patient's hematopoietic progenitor cell population. This might be appropriate, for example, after an individual has undergone chemotherapy. There are certain genetic conditions wherein hematopoietic progenitor cell numbers are decreased, and the methods of the invention may be used in these situations as well.

It also is possible to take the increased numbers of hematopoietic progenitor cells produced according to the invention and stimulate them with hematopoietic growth agents that promote hematopoietic cell maintenance, expansion and/or differentiation, and also influence cell localization, to yield the more mature blood cells, in vitro. Such expanded populations of blood cells may be applied in vivo as described above, or may be used experimentally as will be recognized by those of ordinary skill in the art. Such differentiated cells include those described above, as well as T cells, plasma cells, erythrocytes, megakaryocytes, basophils, polymorphonuclear leukocytes, monocytes, macrophages, eosinohils and platelets.

In all of the culturing methods according to the invention, except as otherwise provided, the media used is that which is conventional for culturing cells. Examples include RPMI, DMEM, Iscove's, etc. Typically these media are supplemented with human or animal plasma or serum. Such plasma or serum can contain small amounts of hematopoietic growth factors. The media used according to the present invention, however, can depart from that used conventionally in the prior art. In particular, it has been discovered, surprisingly, that hematopoietic progenitor cells can be cultured on the matrices described above for extended periods of time without the need for adding any exogenous growth agents (other than those which may be contained in plasma or serum, hereinafter "serum"), without inoculating the environment of the culture with stromal cells and without using stromal cell conditioned media. Prior to the present invention, at least one of the foregoing agents was believed necessary in order to culture hematopoietic progenitor cells.

The growth agents of particular interest in connection with the present invention are hematopoietic growth factors. By hematopoietic growth factors, it is meant factors that influence the survival, proliferation or differentiation of hematopoietic progenitor cells. Growth agents that affect only survival and proliferation, but are not believed to promote differentiation, include the interleukins 3, 6 and 11, stem cell factor and FLT-3 ligand.

Hematopoietic growth factors that promote differentiation include the colony stimulating factors such as GMCSF, GCSF, MCSF, Tpo, Epo, Oncostatin M, and interleukins other than IL-3, 6 and 11. The foregoing factors are well known to those of ordinary skill in the art. Most are commercially available. They can be obtained by purification, by recombinant methodologies or can be derived or synthesized synthetically.

"Stromal cell conditioned medium" refers to medium in which the aforementioned lymphoreticular stromal cells have been incubated. The incubation is performed for a period sufficient to allow the stromal cells to secrete factors into the medium. Such "stromal cell conditioned medium" can then be used to supplement the culture of hematopoietic progenitor cells promoting their proliferation and/or differentiation.

Thus, when cells are cultured without any of the foregoing agents, it is meant herein that the cells are cultured without the addition of such agent except as may be present in serum, ordinary nutritive media or within the blood product isolate, unfractionated or fractionated, which contains the hematopoietic progenitor cells.

According to another aspect of the invention a method for in vivo maintenance, expansion and/or differentiation of hematopoietic progenitor cells is provided. The method involves implanting into a subject a porous solid matrix having seeded hematopoietic progenitor cells, hematopoietic progenitor cell progeny, and lymphoreticular stromal cells. Implantation of matrices similar to the matrices of the invention is well known in the art (Stackpool, G J, et al, Combined Orthopaedic Research Societies Meeting, Nov. 6–8, 1995, San Diego, Calif., Abstract Book p. 45; Turner, T M, et al., 21st Annual Meeting of the Society for Biomaterials, March 18–22, San Francisco, Calif., Abstract Book p. 125). Such matrices are biocompatible (i.e., no immune reactivity-no rejection) and can be implanted and transplanted in a number of different tissues of a subject. Such methods are useful in a variety of ways, including the study of hematopoietic progenitor cell maintenance, expansion, differentiation and/or localization in vivo, in a number of different tissues of a subject, and/or between different subjects.

As used herein, a subject is a human, non-human primate, cow, horse, pig, sheep, goat, dog, cat or rodent. Human hematopoietic progenitor cells and human subjects are particularly important embodiments. As described above, when the matrices of the invention are used for such in vivo implantation studies, biological agents that promote angiogenesis (vascularization) and/or prevent/reduce inflammation may also be used for coating of the matrices. Preferred biological agents are as described above. Also as described above, the hematopoietic progenitor cells are pre-seeded onto the porous solid matrix and cultured in vitro according to the invention, before implantation into a subject. According to the invention, an amount of the cells is introduced in vitro into the porous solid matrix, and co-cultured with lymphoreticular stromal cells in an environment that is free stromal cell conditioned medium, and exogenously added hematopoietic growth factors that promote hematopoietic cell maintenance, expansion and/or differentiation, other than serum. Implantation is then carried out. In certain embodiments, stromal cell conditioned medium and exogenous hematopoietic growth factors may be added during the in vitro culture before implantation.

According to one aspect of the invention, a method for inducing T cell reactivity/activation, in vitro, is provided. Induction of T cell reactivity/activation involves co-culturing the hematopoietic progenitor cells and the lymphoreticular stromal cells in the presence of an antigen, in one of the foregoing matrices, under conditions sufficient to induce the formation of T cells and/or T cell progenitors from the hematopoietic progenitor cells having specificity for the antigen. The foregoing conditions could easily be established by a person of ordinary skill in the art, without undue experimentation (see also Sprent J, et al., *J Immunother*, 1998, 21(3):181–187; Berridge M J, *Crit Rev Immunol*, 1997, 17(2):155–178; Owen M J, et al., *Curr Opin Immunol*, 1996, 8(2):191–198; Whitfield J F, et al., *Moll Cell Biochem*, 1979, 27(3):155–179; Fauci A S, et al., *Ann Intern Med*, 1983, 99(1):61–75).

In important embodiments, antigen presenting cells (preferably mature) are also included in the co-culture of the hematopoietic progenitor cells and the lymphoreticular stromal cells. Antigen stimulation of T cells in the presence of APCs, induces an antigen specific response that can be measured using a proliferation assay or just by measuring IL-2 production (see discussion below). These cells can be detected by culturing T cells with antigen at an appropriate concentration (e.g., 0.1–1.0 μM tetanus toxoid) in the presence of APCs. If antigen specific T cells are present they can be detected using the assays described below under self-tolerance/anergy. Stimulation of T cells in the presence of APCs may include co-stimulation with a co-stimulatory agent. Co-stimulatory agents include lymphocyte function associated antigen-3 (LFA-3), CD2, CD40, CD80/B7-1, CD86/B7-2, OX-2, CD70, and CD82. Co-stimulatory agents may also be used in lieu of APCs, provided that MHC class II molecules and anti-CD3 antibodies are co-administered with the co-stimulatory agent(s).

An antigen, as used herein, falls into four classes: 1) antigens that are characteristic of a pathogen; 2) antigens that are characteristic of an autoimmune disease; 3) antigens that are characteristic of an allergen; and 4) antigens that are characteristic of a tumor. Antigens in general include polysaccharides, glycolipids, glycoproteins, peptides, proteins, carbohydrates and lipids from cell surfaces, cytoplasm, nuclei, mitochondria and the like.

Antigens that are characteristic of pathogens include antigens derived from viruses, bacteria, parasites or fungi. Examples of important pathogens include *vibrio choleras*, enterotoxigenic *Escherichia coli*, rotavirus, *Clostridium difficile, Shigella* species, *Salmonella typhi*, parainfluenza virus, influenza virus, *Streptococcus pneumonias, Borella burgdorferi*, HIV, *Streptococcus mutans, Plasmodium falciparum, Staphylococcus aureus*, rabies virus and Epstein-Barr virus.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae; and viruses including, but not limited to, cytomegalovirus; Hepatitis A,B,C, D, E; Herpes simplex virus types 1 & 2; Influenzae virus; Mumps virus; Parainfluenza 1, 2 and 3; Epstein Barr virus; Respiratory syncytial virus; Rubella virus; Rubeola virus; Varicella-zoster virus; Vibrio Cholerae; Human immunodeficiency viruses (HIVs) and HIV peptides, including HIV-1 gag, HIV-1 env, HIV-2 gag, HIV-2 env, Nef, RT, Rev, gp120, gp41, p15, p17, p24, p7-p6, Pol, Tat, Vpr, Vif, Vpu; Hantavirus; Ebola virus; Lymphocytic ChorioMeningitis virus; Dengue virus; Rotavirus; Human T-lymphotropic (HTLV-I); HTLV-II; Human herpesvirus-6 (HHV-6); HHV-8; Guanarito virus; *Bartonella henselae;* Sin nombre virus; and Sabia virus. Exemplary cytomegalovirus epitopes include GP 33–43, NP396–404, and GP276–286. An exemplary influenza epitope includes the HA peptide.

Bacteria in general include but are not limited to: *P. aeruginosa; Bacillus anthracis; E. coli, Enterocytozoon bieneusi; Klebsiella* sp.; *Klebsiella pneumoniae; Serratia* sp.; *Pseudomonas* sp.; *P. cepacia; Acinetobacter* sp.; *S. epidermis; E. faecalis; S. pneumoniae; S. aureus; Haemophilus* sp.; *Haemophilus* Influenza; *Neisseria* Sp.; *Neisseria gonorheae; Neisseria meningitis; Helicobacter pylori; Bacteroides* sp.; *Citrobacter* sp.; *Branhamella* sp.; *Salmonella* sp.; *Salmonella typhi; Shigella* sp.; *S. pyogenes; Proteus* sp.; *Clostridium* sp.; *Erysipelothrix* sp.; *Lesteria* sp.; *Pasteurella multocida; Streptobacillus* sp.; *Spirillum* sp.; *Fusospirocheta* sp.; *Actinomycetes; Mycoplasma* sp.; *Chlamydiae* sp.; *Chlamydia trachomatis; Campylobacter jejuni; Cyclospora cayatanensis; Rickettsia* sp.; *Spirochaeta*, including *Treponema pallidum* and *Borrelia* sp.; *Legionella* sp.; *Legionella pneumophila; Mycobacteria* sp.; *Mycobacterium* tuberculosis; *Ureaplasma* sp.; *Streptomyces* sp.; *Trichomonas* sp.; and *P. mirabilis*, as well as toxins, that include, but are not limited to, Anthrax toxin (EF); Adenylate cyclase toxin; Cholera enterotoxin; *E. coli* LT toxin; *Escherichia coli* 0157:H7; Shiga toxin; Botulinum Neurotoxin Type A heavy and light chains; Botulinum Neurotoxin Type B heavy and light chains; Tetanus toxin; Tetanus toxin C fragment; Diphtheria toxin; Pertussis toxin; Parvovirus B19; *Staphylococcus* enterotoxins; Toxic shock syndrome toxin (TSST-1); Erythrogenic toxin; and *Vibrio cholerae* 0139.

Parasites include but are not limited to: *Ehrlichia chafeensis; Babesia; Encephalitozoon cuniculi; Encephalitozoon hellem*; Schistosoms; *Toxoplasma gondii; Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidum parvum; Pneumocytis carinii, Babesia bovis, B. divergens, B. microti, Isospore belli, L hominis; Dientamoeba fragiles; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirius pubis*; and *Dermatobia hominis.*

Fungi in general include but are not limited to: *Cryptococcus neoformans; Blastomyces dermatitidis; Aiellomyces dermatitidis; Histoplasfria capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata;* and *Dermatophyres* species.

Antigens that are characteristic of autoimmune disease typically will be derived from the cell surface, cytoplasm, nucleus, mitochondria and the like of mammalian tissues.

Examples include antigens characteristic of uveitis (e.g. S antigen), diabetes mellitus, multiple sclerosis, systemic lupus erythematosus, Hashimoto's thyroiditis, myasthenia gravis, primary myxoedema, thyrotoxicosis, rheumatoid arthritis, pernicious anemia, Addison's disease, scleroderma, autoimmune atrophic gastritis, premature menopause (few cases), male infertility (few cases), juvenile diabetes, Goodpasture's syndrome, pemphigus vulgaris, pemphigoid, sympathetic opthalmia, phacogenic uveitis, autoimmune haemolytic anemia, idiopathic thrombocylopenic purpura, idiopathic feucopenia, primary biliary cirrhosis (few cases), ulcerative colitis, Siogren's syndrome, Wegener's granulomatosis, poly/dermatomyositis, and discold lupus erythromatosus.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include the urushiols (pentadecylcatechol or heptadecyicatechol) of *Toxicodendron* species such as poison ivy, poison oak and poison sumac, and the sesquiterpenoid lactones of ragweed and related plants.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and tumor mucins and glycolipids. Tumors include, but are not limited to, those from the following sites of cancer and types of cancer: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogeneous leukemia; multiple myeloma; AIDS associates leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basal cell cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. Viral proteins associated with tumors would be those from the classes of viruses noted above. Antigens characteristic of tumors may be proteins not usually expressed by a tumor precursor cell, or may be a protein which is normally expressed in a tumor precursor cell, but having a mutation characteristic of a tumor. An antigen characteristic of a tumor may be a mutant variant of the normal protein-having an altered activity or subcellular distribution. Mutations of genes giving rise to tumor antigens, in addition to those specified above, may be in the coding region, 5' or 3' noncoding regions, or introns of a gene, and may be the result of point mutations frameshifts, deletions, additions, duplications, chromosomal rearrangements and the like. One of ordinary skill in the art is familiar with the broad variety of alterations to normal gene structure and expression which gives rise to tumor antigens.

Specific examples of tumor antigens include: proteins such as Ig-idiotype of B cell lymphoma, mutant cyclin-dependent kinase 4 of melanoma, Pmel-17 (gp 100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma; carbohydrate/lipids such as muci mucin of breast, pancreas, and ovarian cancer, GM2 and GD2 gangliosides of melanoma; oncogenes such as mutant p53 of carcinoma, mutant ras of colon cancer and HER21neu proto-onco-gene of breast carcinoma; viral products such as human papilloma virus proteins of squamous cell cancers of cervix and esophagus; and antigens (shown in parenthesis) from the following tumors: acute lymphoblastic leukemia (etv6; am11; cyclophilin b), glioma (E-cadherin; α-catenin; β-catenin; γ-catenin; pl20ctn), bladder cancer (p21ras), billiary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)--C017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), hodgkins lymphoma (Imp-1; EBNA-1), lung cancer (CEA; MAGE-3; NY-ESO-1), lymphoid cell-derived leukemia (cyclophilin b), myeloma (MUC family; p21ras), non-small cell lung carcinoma (HER2/neu; c-erbB-2), nasopharyngeal cancer (imp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), testicular cancer (NY-ESO-1), T cell leukemia (HTLV-1 epitopes), and melanoma (Melan-A/MART-1; cdc27; MAGE-3; p21ras; gp100$^{Pme}$1117). It is also contemplated that proteinaceous tumor antigens may be presented by HLA molecules as specific peptides derived from the whole protein. Metabolic processing of proteins to yield antigenic peptides is well known in the art; for example see U.S. Pat. No. 5,342,774 (Boon et al.). and the ones on the lists previously.

Antigens may also include: C reactive protein; Coxsackie B1, B2, B3, B4, EI5, B6 proteins; Myelin basic protein; pancreatic beta-cell antigens; arthritis associated antigens (cartilage, aggrecan, type II collagen); AP-1; NF-kappaB; desmoglein (Dsg 1 or 3); and alzheimer's associated antigens (prions, amyloid-beta protein), and/or any synthetic agent that binds to the T-cell receptor.

Further exemplary cancer, viral, and beta islet autoantigens are described below in Tables 2, 3, and 4 respectively.

TABLE 3

Exemplary Viral Antigens

| Protein | MHC | Peptide | Position | SEQ ID NO: |
|---|---|---|---|---|
| Rubella E1 | | WVTPVIGSQARKCGL | 276–290 | 38 |
| | | RVIDPAAQ | 412–419 | 39 |
| Measles F | | HQALVIKLMPNITLL | | 40 |
| Papilloma | | RLCVQSTHV | | 41 |
| | | YVRDGNPYA | E6 60–68 | 42 |
| | | GYNKPLCDLL | E6 98–107 | 43 |
| Influenza matrix | | KGILGFVFTLTV | 57–68 | 44 |
| influenza HA | | EKYVKQNTLKLAT | 307–319 | 45 |
| Hepatitis B | | WLSLLVPFV | | 46 |
| SAg | | FLGGTTVCL | | 47 |
| Hepatitis C NS | | YLVAYQATV | | 48 |
| NS3 | | GLRDLAVAV | | 49 |
| | | GYKVLVLNPSVAAT | 1248–1261 | 50 |
| | | KLVALGINAV | 1406–1415 | 51 |
| Tetanus | | QYIKANSKFIGIYQL | 830–843 | 52 |

TABLE 2

Exemplary Cancer Antigens

| Protein | MHC | Peptide | Position | SEQ ID NO: |
|---|---|---|---|---|
| MAGE-A1 | HLA-A1 | EADPTGHSY | 161–169 | 1 |
| | HLA-Cw16 | SAYGEPRKL | 230–238 | 2 |
| MAGE-A3 | HLA-A1 | EVDPIGHLY | 168–176 | 3 |
| | HLA-A2 | FLWGPRALV | 271–279 | 4 |
| | HLA-B44 | MEVDPIGHLY | 167–176 | 5 |
| MAGE-A6 | HLA-Cw16 | KISGGPRISYPL | 292–303 | 6 |
| MAGE melanoma AG | | ALSRKVAEL | | 7 |
| BAGE | HLA-Cw16 | AARAVFLAL | 2–10 | 8 |
| GAGE-1,2 | HLA-Cw16 | YRPRPRRY | 9–16 | 9 |
| RAGE | HLA-B7 | SPSSNRIRNT | 11–20 | 10 |
| GnT-V | HLA-A2 | VLPDVFIRC | 2–10/11 | 11 |
| MUM-1 | HLA-B44 | EEKLIVVLF | exon 2/intron | 12 |
| | | EEKLSVVLF (wild type) | | 13 |
| CDK4 | HLA-A2 | ACDPHSGHFV | 23–32 | 14 |
| | | ARDPHSGHFV (wild type) | | 15 |
| β-catenin | HLA-A24 | SYLDSGIHF | 29–37 | 16 |
| | | SYLDSGIHS (wild type) | | 17 |
| Tyrosinase | HLA-A2 | MLLAVLYCL | 1–9 | 18 |
| | HLA-A2 | YMNGTMSQV | 369–377 | 19 |
| | HLA-A2 | YMDGTMSQV | 369–377 | 20 |
| | HLA-A24 | AFLPWHRLF | 206–214 | 21 |
| | HLA-B44 | SEIWRDIDF | 192–200 | 22 |
| | HLA-B44 | YEIWRDIDF | 192–200 | 23 |
| | HLA-DR4 | QNILLSNAPLGPQFP | 56–70 | 24 |
| | HLA-DR4 | DYSYLQDSDPDSFQD | 448–462 | 25 |
| | HLA-A2 | ILTVILGVL | 32–40 | 26 |
| gp100$^{Pmel117}$ | HLA-A2 | KTWGQYWQV | 154–162 | 27 |
| | HLA-A2 | ITDQVPFSV | 209–217 | 28 |
| | HLA-A2 | YLEPGPVTA | 280–288 | 29 |
| | HLA-A2 | LLDGTATLRL | 457–466 | 30 |
| | HLA-A2 | VLYRYGSFSV | 476–485 | 31 |
| PRAME | HLA-A24 | LYVDSLFFL | 301–309 | 32 |
| NY-ESO-1 | HLA-A2 | SLLMWITQCFL | 157–167 | 33 |
| | HLA-A2 | SLLMWITQC | 157–165 | 34 |
| | HLA-A2 | QLSLLMWIT | 155–163 | 35 |
| c-erb2 | | HLYQGCQVVPLTSIISAV | | 36 |
| p53 | 264–272 | LLGRNSFEV | | 37 |

TABLE 4

Exemplary Beta Islet Cell Autoantigens:

| Protein | Peptide | Position | SEQ ID NO: |
|---|---|---|---|
| glutamic acid decarboxylase 65 | TYELAPVFVLLEYVT | 206–220 | 53 |
|  | LKKMRFIIGWPGGSG | 221–235 | 54 |
|  | KKGAAAIGIGTDSVI | 286–300 | 55 |
|  | PLOCSALLVREEGLM | 401–415 | 56 |
|  | WLMWRAKGTTGFEAH | 456–470 | 57 |
| tyrosine phosphatase IA-2 | VIVMLTPLVEDGVKQC | 805–820 | 58 |

One or more antigens can be used at the same time for incubation in the foregoing culture system. Preferably, the lymphoreticular stromal cells are thymic stromal cells and of murine origin when the hematopoietic progenitor cells being expanded are human. Therefore, large numbers of antigen-specific mature T and immature T cells may be obtained in a short period of time that were never before realized using existing art methodologies. The present invention thus becomes useful in a wide range of applications, including pre-exposure vaccination of individuals with in vitro primed T cells, treatment of cancer patients using tumor-targeted T cell immunotherapy, treatment of bone marrow transplant patients (for whom opportunistic infections, such as CMV, are problematic and yet amenable to treatment with targeted T cells such as CMV-targeted cytotoxic lymphocytes), enhancement of conventional vaccination efficacy through T cell adjuvant therapy, treatment of outbreaks of emergent or re-emergent pathogens, etc. The antigen presenting cells include cells such as dendritic cells, monocytes/macrophages, Langerhans cells, Kupfer cells, microglia, alveolar macrophages and B cells, and methods for their isolation are well known in the art. The antigen presenting cells may also be derived from hematopoietic progenitor cells in vitro.

Immunological tolerance refers to the inhibition of a subject's ability to mount an immune response, e.g., to a donor antigen, which would otherwise occur in response to the introduction of a non-self antigen into the subject. Tolerance can involve humoral, cellular, or both humoral and cellular responses. Thymic education results in the generation of T cells capable of responding to a myriad of foreign antigens in the context of self-MHC, but not self-antigens alone. This is achieved primarily by a systematic rescue of appropriate thymocytes from programmed cell death, based on a theme of self-restriction, and the release of these cells into the periphery to serve as self-tolerant T cells.

Methods of the invention are useful, inter alia, for generating large numbers of lymphoid tissue-specific cells that are educated toward specific cells/antigens, and are therefore tolerant toward the specific cells/antigens. For example, according to the invention and in the context of transplantation, a recipient's hematopoietic progenitor cells are co-cultured, in one instance, with a donor's lymphoreticular stroma and/or a donor's antigen presenting cells. The lymphoid tissue-specific cells that are generated from such co-culture are educated toward donor's cells/antigens and are therefore tolerant, thus increasing the likelihood of a successful transplantation of an donor organ into a recipient (host). Various other permutations are therefore contemplated by the invention (see summary), where non-autologous cells (e.g., donor cells) can be co-cultured in the presence of other non-autologous or autologous (e.g., recipient) cells. Non-autologous cells, as discussed earlier, are cells that originate from a different subject (see earlier discussion). They can be from a single source (e.g., hematopoietic progenitor cells and lymphoreticular cells from one subject), or from multiple sources (e.g., two different subjects -hematopoietic progenitor cells from one subject and lymphoreticular cells from another subject).

Exemplary permutations include:

| Prog. cell source | Non-autologous* progenitor cells | | | | Autologous (Recipient) progenitor cells | | | |
|---|---|---|---|---|---|---|---|---|
| Stroma source | Non-autologous stroma | | Recipient stroma | | Non-autologous stroma | | Recipient stroma | |
| APC source | Non-autologous APCs | Recipient APCs | Non-autologous APCs | Recipient APCs | Non-autologous APCs | Recipient APCs | Non-autologous APCs | Recipient APCs |

*can be from one source or multiple sources

Self-tolerance can be established in vitro under conditions known in the art that include coculturing $CD34^+$ T progenitors derived from a donor (A), in the presence of thymic stroma from another individual (B). Briefly, thymic stroma is established from freshly isolated thymic tissue that is digested into a single cell suspension using a collagenase (20 μg/ml, Sigma Chemical Co.). Thymic stromal cultures are established by plating the cell suspension in 24 well plates at a concentration of $4 \times 10^6$ viable cells per well in a volume of 2 ml R10 (RPMI plus 10% FCS). Cultures are incubated in a standard humidified tissue culture incubator at 37° C. with 5% $CO_2$. After one to two days, non-adherent cells are removed by washing three times with R10. The stroma requires an additional 7–10 days to become confluent. The stroma is maintained in R10 which is changed at least twice per week. After 7–10 days in culture, $CD34^+$ cells in R10 are added to the stroma at a concentration of $1-3 \times 10^5$ cells per well. Cultures are fed bi-weekly using partial medium exchanges with R10 with no exogenous cytokines added to these cultures. After 14–21 days, the non-adherent cells are removed from the cultures. The remaining, attached cells are self-tolerant T cells that have developed in vitro.

Methods for determining if tolerance has been established in vitro are also known to a person of ordinary skill in the art, and involve measurement of a proliferative response to: self (A), as well as to the thymus donor (B), and a third party (C), peripheral blood mononuclear cells (PBMCs). Briefly, PBMCs from A, B and C are prepared by Ficoll® gradient centrifugation.

$1 \times 10^5$ responder cells (in vitro generated T cells from A) are plated out in multiple replicates in a 96 well plate. Stimulator cells (PBMCs from A, B and C) are irradiated (3000 Rads) and added in 12 replicates at $1 \times 10^5$ cells per well. Con-A (5 μg/ml) is used as a positive control. After 4 days 1 μCi of $^3$H-Thymidine is added to each well, and the plates harvested 18–24 hours later. If tolerance has been established, the in vitro generated T cells will respond and proliferate when mixed with an unrelated third party (C), but do not proliferate when mixed with PBMCs from self (A) or the thymic donor (B).

According to another aspect of the invention, a method for inducing T cell anergy, in vitro, is provided. Induction of T cell anergy involves co-culturing the hematopoietic progenitor cells and the lymphoreticular stromal cells in one of the foregoing matrices, in the presence of antigen under conditions sufficient to induce the formation of T cells and/or T cell progenitors and to inhibit activation of the formed T cells and/or T cell progenitors.

Anergy is defined as an unresponsive state of T cells (that is they fail to produce IL-2 on restimulation, or proliferate when restimulated)(Zamoyska R, *Curr Opin Immunol*, 1998, 10(1):82–87; Van Parijs L, et al., *Science*, 1998, 280(5361):243–248; Schwartz R H, *Curr Opin Immunol*, 1997, 9(3):351–357; Immunol Rev, 1993, 133:151–76). Anergy may, however, be irreversible. Anergy may be induced via antigen-specific T cell stimulation in the absence of co-stimulation (one signal vs. two signal hypothesis). Alternatively peptides of low affinity or very high concentrations of peptide even in the presence of co-stimulation can induce anergy. Anergy can be induced in vitro by culturing T cells in the absence of antigen presenting cells (B cells, macrophages or dendritic cells). These T cells are then exposed to antigen for example tetanus toxoid (e.g., 0.1–1.0 μM). An aliquot of the T cells is used to present antigen. This constitutes antigen presentation without co-stimulation and will induce anergy (Nelson A, et al., *In Immuno*, 1998, 10(9):1335–46). Alternatively T cells can be cocultured with APCs, in the context of very high (10–100 μM) or very low (0.01–0.05 μM) tetanus toxoid, which will induce a state of unresponsiveness.

Anergy can be measured by taking the T cells described above, and restimulating them with antigen (e.g., 0.1–1.0 μM tetanus toxoid) in the presence of APCs. If the cells are anergic they will not respond to antigen at an appropriate concentration in the context of APCs. Anergy is measured by culturing the cells as such for 3–5 days and measuring proliferation or the lack thereof as follows. Briefly APCs are plated out in multiple replicates in a 96 well plate, after irradiation (3000 Rads). These cells are pulsed with antigen (e.g., 0. 1–1.0 μM) for 2 hours, and then T cells are added in 12 replicates at $1\times10^5$/cells per well. Con-A (5 μg/ml) is used as a positive control. After 4 days 1 μCi of $^3$H-Thymidine is added to each well, and the cells are harvested 18–24 hours later. If the cells are anergic they will not proliferate in response to antigen stimulation. Alternatively, the production of IL-2 can be measured in the supernatants of the cultures described above. Supernatants are collected daily and IL-2 production is measured using a commercial ELISA assay. An additional approach includes flow cytometry based staining specific for intracellular expression of the cytokines IL-2, γIFN and TNFα using antibodies specific to the human forms of these factors (Becton Dickinson). Further, semiquantitative RT-PCR of mRNA for these factors can also be used.

According to another aspect of the invention, a method for identifying an agent suspected of affecting hematopoietic cell development is provided. The method involves introducing an amount of hematopoietic progenitor cells and an amount of lymphoreticular stromal cells into a porous, solid matrix of the invention, and co-culturing in a test co-culture the hematopoietic progenitor cells and the lymphoreticular stromal cells in the presence of at least one candidate agent suspected of affecting hematopoietic cell development. By "hematopoietic cell development" it is meant to include hematopoietic progenitor cell maintenance, expansion, differentiation, and/or cell-death apoptosis (programmed cell-death). "Maintenance" includes the hematopoietic progenitor cell's ability to maintain its pluripotentiality. "Expansion" includes the hematopoietic progenitor cell's ability to divide and grow, and "differentiation" includes the hematopoietic progenitor cell's ability to differentiate toward a specific cell lineage. "Cell-death" also includes programmed cell-death (apoptosis). By "affecting" hematopoietic cell development it is therefore meant to include effects on hematopoietic progenitor cell maintenance, expansion, differentiation, and/or cell-death. Such effect (or influence) can be either positive or negative/inhibitory in nature. For example, a positive effect would be maintenance of pluripotentiality of the progenitor cells, and/or increase in the number of the pluripotential progenitor cells. A negative effect would lead into the differentiation of the progenitor cells and loss of pluripotentiality, or even progenitor cell-death. A negative effect on a particular cell population may also have a positive effect on a different cell population. For example, an inhibitory effect on a B cell lineage may result in a positive effect on, for example, a T cell lineage. The agent suspected of affecting hematopoietic cell development may be administered in the form of a transfected nucleic acid into the lymphoreticular stromal cells as well as being added straight into the media.

To determine whether the at least one candidate agent affects hematopoietic cell development in the test co-culture, the phenotype and/or genotype (as well as the numbers) of the hematopoietic cells generated in the test co-culture is compared to the phenotype and/or genotype (and numbers) of hematopoietic cells generated in a control co-culture. The control co-culture is performed under identical conditions to the test co-culture (i.e., identical initial numbers and types of both hematopoietic progenitor cells and lymphoreticular stromal cells, in an identical matrix, identical culture media, etc.), but with the exception that the at least one candidate agent suspected of affecting cell hematopoietic cell development is omitted from the control co-culture. Methods for determining the phenotype and/or genotype of hematopoietic cells are well known in the art, and a few examples can be found throughout this application.

In yet another aspect of the invention, a method for isolating from a cell culture an agent suspected of affecting hematopoietic cell development is also provided. The method involves introducing an amount of hematopoietic progenitor cells and an amount of lymphoreticular stromal cells into a porous, solid matrix of the invention, co-culturing the hematopoietic progenitor cells and the lymphoreticular stromal cells and obtaining a test-supernatant (or a fraction thereof) from the co-culture. The test-supernatant (or a fraction thereof) is then compared to a control-supematant (or a fraction thereof). By "comparing" it is meant that a profile of agents (suspected of affecting hematopoietic cell development) present in the test-supernatant and secreted from the cells of the co-culture, is compared to a similar profile of agents present in the control-supernatant and secreted from the cells of a control culture or co-culture. Methods of obtaining such profiles of secreted agents are well known in the art and include two-dimensional (2-D) gel electrophoresis. Other methods also include various types of HPLC, thin layer chromatography.

A "control culture or co-culture" may involve the culture of hematopoietic progenitor cellsin a parallel culture system known in the art (e.g. U.S. Pat. No. 5,677,139 by Johnson et al.), in order to obtain a result that correlates (i.e. approximates) to the result established in the co-culture system of the invention. For example, a test co-culture according to the invention that involves the co-culture of human hematopoietic progenitor cells and lymphoreticular stromal cells from a mouse thymus, gives rise to a diverse (a variety of sub-types) population of human lymphoid cells committed to the T cell lineage. The test-supernatant obtained from such co-culture is then compared to a control-supernatant obtained from a culture of human hematopoietic progenitor cells in a parallel system of the prior art (as described above) that also gives rise to a population of human lymphoid cells committed to the T cell lineage. Other examples of control cultures or co-cultures may include the co-culture of hematopoietic progenitor cells with lymphoreticular stromal cells of different tissue origin to the ones used in the test co-culture in the matrix of the invention. Additionally, the tissue may or may not be of lymphoid origin. A person of ordinary skill in the art would be able to easily choose and establish such control cultures or co-cultures. Once the profiles of agents suspected of affecting hematopoietic cell development are obtained, a subfraction of the test-supernatant that contains an agent suspected of affecting hematopoietic cell development that appears to be different or absent from the control-supernatant, can then be isolated and further characterized. For example, a candidate agent that appears to be migrating differently in a 2-D gel electrophoresis blot of the test-supernatant can be purified and further characterized using methods such as protein sequencing and mass spectrometry. Agents that appear in the 2-D gel electrophoresis blot but are absent from the blot of the test-supernatant are also suspect of affecting hematopoietic cell development and can be further purified.

The invention will be more fully understood by reference to the following examples. These examples, however, are merely intended to illustrate the embodiments of the invention and are not to be construed to limit the scope of the invention.

EXAMPLES

Experimental Procedures

Isolation of Human CD34$^+$ Cells

Five to ten milliliters of venous umbilical cord blood (UCB) was extracted using a heparinized syringe prior to the severing of the umbilical cord during a Caesarean section delivery of a human embryo. After the umbilical cord was severed and the infant delivered, the placenta was removed by clamping the umbilical vein proximally and severing distally to the placenta. Immediately after the placenta was removed the umbilical vein was unclamped and the blood contained in the placenta drained into an appropriate heparinized container. Before processing, the cord and placenta blood was mixed together. After extraction the cord/placenta blood was diluted 2:1 with washing media (RPMI 1640, 10 IU/ml penicillin, 10 µg/ml streptomycin, 1 mM L-glutamine). The sample(s) were then underlayed with a volume of Ficoll-Hypaque® (1.077 g/ml) equal to half of the diluted sample volume so that a distinct sample/Ficoll interface formed. After centrifugation for 45 minutes at 400× g the interface containing mononuclear cells was removed. The cells were then washed by resuspending in culture medium and centrifuging for 10 minutes at 400× g. The resulting pellet was resuspended in 6 ml of ammonium chloride lysing buffer (0.15M $NH_4Cl$, 1.0 mM $KHCO_3$, 0.1M $Na_2EDTA$) for 3 minutes to lyse any remaining erythrocytes. The suspension was then diluted with media and washed twice more. After the final wash the cells were resuspended in 1–2 ml media and the number of viable cells was determined by trypan blue exclusion.

Human CD34$^+$ progenitor cells were also prepared from disaggregated human fetal thymus obtained from 16–22 week old abortuses. For dissagregation procedures see below under Mouse Thymic Stroma.

Cells expressing the surface antigen CD34 were isolated using the Dynal® CD34 Progenitor Cell Selection System (Dynal, Lake Success, N.Y.) or the MiniMACS system (Miltenyi Biotec, Bergisisch Gladbach, Germany). The mononuclear cells isolated from UCB (or bone marrow) were suspended in isolation buffer (PBS, 2% heat inactivated fetal bovine serum, 10 IU/ml penicillin, 10 µg/ml streptomycin) at a concentration of $2.5 \times 10^7$ cells/ml. The suspension was then added to magnetic anti-human CD34 beads (Dynal® M-450 CD34) in a ratio of $4.0 \times 10^7$ beads per ml of suspension, in a round bottom tube. (Dynabeads® M-450 CD34 are superparamagnetic beads bound to monoclonal antibody specific for CD34). The mixture was vortexed gently and incubated at 4° C. for 45 minutes with gentle tilt rotation using a Dynal® Sample Mixer. After incubation the bead/cell mixture was resuspended in a larger volume of isolation buffer and placed in a magnetic separation device for 2 minutes to allow the cell/bead complexes to accumulate to the tube wall. While still exposed to the agent, the suspension containing the cells not bound to the magnetic beads was aspirated. The cell/bead complexes were washed three more times in this manner, pooling the suspensions containing the CD34 negative cells into the same tube. The tube containing the released cells (CD34−) was then placed on the magnetic separator to remove any remaining beads and this supernatant was transferred to a new conical tube. All CD34$^+$ cells attached to beads were washed twice in a minimum of 10 ml of isolation buffer with centrifugation at 2000 rpm for 8 min. Cells bound to magnetic beads were then resuspended in 100 µl of isolation buffer per $4 \times 10^7$ beads used, with a minimum volume of 100 µl. The CD34 positive cells were then detached from the beads by adding an equal volume of an anti-idiotype antibody (DETACHaBEAD® CD34, Dynal), vortexing, and gently mixing at room temperature using a Dynal Sample Mixer for one hour. The cells were isolated from the cell/bead suspension by adding isolation buffer and placing the tube in the magnetic separation device for 2 minutes. After the beads migrated to the tube wall, the supernatant containing the CD34 positive cells was transferred to a new tube. The beads were washed three more times with the suspensions containing the released cells pooled into the same tube. The tube containing the released CD34+ cells was then placed on the magnetic separator to remove any remaining beads, and the supernatant was transferred to a new conical tube. The cells were washed twice in a minimum of 10 ml of isolation buffer with centrifugation at 2000 rpm for 10 minutes.

Alternatively, human bone marrow was obtained by posterior iliac crest aspiration from healthy adult volunteers in accordance with institutional review board guidelines and after giving informed consent. 10–15 mL of human bone marrow was collected in an heparinized sterile syringe, transported at room temperature and used within 6 hours. Bone marrow was diluted in a 5-times volume of PBS and the mononuclear cells (MNCs) separated by density gradient centrifugation over a column of Ficoll-Paque® (Pharmacia Biotech Inc., Piscataway, N.J.). MNCs thus obtained were washed twice in 10 mL PBS, and the remaining erythrocytes removed by lysis with ACK Lysing Buffer (Bio Whittaker, Walkersville, Md.).

In order to select a more immature phenotype of progenitor cell within the CD34$^+$ population, we elected to use an immunomagnetic bead selection system employing an antibody to the novel stem cell antigen, AC133. AC133 is a 5-transmembrane cell surface antigen expressed on 20–60% of human CD34$^+$ cells, including the CD38$^{neg/dim}$ subset (representing the non-lineage-committed precursors) but is not expressed on mature leukocytes (Yin A H, et al., *Blood,* 1997. 90:5002–12; Nfiraglia S, et al., *Blood,* 1997, 90: 5013–21; Buhring H J, et al., *Ann N Y Acad Sci,* 1999, 872: 25, discussion 38–9). Although a small number of mature CD2$^+$ T-cells were transferred into our co-cultures with the AC133$^+$ progenitors we do not believe that the T-cells generated in this system are derived from either CD2$^+$ mature lymphocytes or CD2$^+$ lymphoid-committed precursors. We, and others (Fisher A G, et al., *Int Immunol,* 1990, 2:571–8), have observed that the deliberate introduction of mature human T-cells into the co-cultures does not result in increased numbers of T-cells or their precursors. The AC133$^+$ MNC fraction was isolated by immunomagnetic bead selection using an AC133 Cell Isolation Kit (Miltenyi Biotec Inc., Auburn, Calif.) according to the manufacturer's protocols.

Mouse Thymic Stroma:

Thymi were obtained from freshly sacrificed 6 week-old B6 (BALB/C) mice. Thymi were physically disaggregated with surgical scissors in order to produce a cell suspension which also contained fragments of thymic tissue less than 0.5 mm$^3$ in size. The cell suspension containing thymic fragments was plated onto 0.5 cm×0.5 cm×0.2 cm pieces of Cellfoam (80 ppi), placed in each well of a 24 well plate. Each well contained at least 5×10$^6$ cells and 4 fragments of fetal thymus per Cellfoam block and the cells were cultured in fully supplemented IMDM. The medium in thymic cultures was changed initially at 48 hours post establishment of the culture and at three day intervals there after. On average 80% confluent thymic stromal monolayers were established on Cellfoam between 10 and 14 days. At 10 to 14 days of culture the Cellfoam blocks each containing a sub-confluent layer of thymic stroma were removed from the 24 well plate and placed in the wells of a new 24 well plate, and co-cultured with CD34$^+$ cells.

Human CD34$^+$/Murine Thymic Stroma Co-Culture Conditions:

Five thousand CD34$^+$ cells derived from UCB or human bone marrow were then plated onto the irradiated murine thymic stroma. In the case where Cellfoam was used, CD34$^+$ cells were plated directly onto the Cellfoam itself in the well of the 24 well tissue culture dish. Medium in co-cultures was changed every three days and was not supplemented with exogenous cytokines. Cells generated from the CD34$^+$ cells were harvested at 7 days post establishment of the co-culture and flow-cytometric and functional studies were performed on the derived cells.

Assessment of Immunophenotype and Function of Cells Derived from the Co-Cultures:

Adherent cells were harvested with a non-trypsin isolation solution (Cell Dissociation Solution, Sigma, St. Louis, Mo.) to minimize alteration of surface staining characteristics. To recover adherent cells from Cellfoam, units were washed twice by immersion into PBS, saturated by brief vortexing in an excess of Cell Dissociation Solution, incubated for 20 minutes at 37° C., and centrifuged at 1500 rpm for 10 minutes.

Cells were harvested by gentle aspiration and washed twice in PBS. Harvested cells were counted and assessed for viability by trypan blue exclusion. After counting, cells were stained in a final volume of 100 μL with 2% mouse serum (Dako, Carpentiera, Calif.) and the following fluorochrome-conjugated antibodies: TCRαβ, TCRγδ, CD2, CD3, CD4, CD8, CD14, CD33 and CD34 (Becton Dickinson, San Jose, Calif.). Conjugated isotype control antibodies for all four fluorochromes (FITC, PE, Peridinin chlorophyll protein (PerCP), and Allophycocyanin (APQ) were used for each culture. Stained samples were washed three times with PBS, fixed with 1% paraformaldehyde, and analyzed with a FACScalibur® flow cytometer (Becton Dickinson). Appropriate controls included matched isotype antibodies to establish positive and negative quadrants, as well as appropriate single color stains to establish compensation. For each sample, at least 10,000 list mode events were collected. Anti-CD3 and anti-CD14 were utilized to detect contaminating T-cells and monocytes in the CD34+ selected MC subpopulation.

Human leukocytes were distinguishable from murine cells on immunophenotypic analysis by gating on the CD45$^+$ population. After 14 days in co-culture, >70% of CD45$^+$ cells coexpressed CD3, CD4, and/or CD8. It was possible to track the sequential differentiation of T-lymphoid precursors in this system over 2 weeks (FIG. 1). CD34$^+$ progenitors added into co-culture with a murine thymic stroma cells, on a three-dimensional matrix (Cellfoam). Non-adherent cells were harvested 7, 14 and 21 days after establishment of the co-cultures and their immunophenotype determined by FACS analysis. The data in panel (a) demonstrate the acquisition of CD2 and the down-regulation of the hematopoietic progenitor cell marker, CD34. Acquisiton of cell surface CD4 and CD8 markers occurred after 14 days in coculture; (b): discrete populations of SP CD4$^+$ and SP CD8$^+$ are demonstrated including their DP CD4$^+$CD8$^+$ precursors. Acquisition of CD4 at day 14 was associated with acquisiotion of CD3; (c and d): all CD4$^+$ cells co-expressed CD3. CD3 was co-expressed with the majority of CD8$^+$ cells; those cells which were CD3$^-$CD8$^+$ were found to express TCRγδ. TCRαβ was expressed by 78% of CD3$^+$ cells although a smaller population (20%) of CD3+ cells expressing TCRγδ was also detectable (6% CD3$^+$CD8$^+$ TCRγδ, 14% CD3$^+$CD8$^+$ TCRγδ).

T cell Function:

T cell function was assessed by determining CD69 expression in response to mitogens and $^3$H-Thymidine uptake in response to the mitogen Con-A. T cells generated in the co-culture system were also examined for their infectability by HIV-1 and their transducability by the MFG murine retroviral vector. T cells generated from the co-culture showed expected high levels of $^3$H-Thymidine uptake (10× control unresponsive cells) in response to the mitogen ConA and a four-fold increase in the expression of the activation marker CD69 as determined by flow cytometry.

HIV-1 Challenge of T-Cells Generated from HPC/Thymic Stromal Co-Cultures:

T-cells generated from HPCs were challenged with T-cell tropic isolate HIV$_{IIIB}$ at a multiplicity of infection of 1. Titered stocks of HIV-1 were generated by standard means well known in the art. Samples of culture supernatant were removed from cultures at 3, 6, 9, 14 and 28 days post HIV challenge for HIV-1 p24 antigen estimation by ELISA (Coulter, Miami, Fla.). Secondly, sorted CD4+ T cells generated from co-cultures of BM HPCs with thymic stroma were challenged with HIV$_{IIIB}$ at a multiplicity of infection of 1. Cell viability was also determined following challenge of monocytes and T cells with HIV-1 using trypan blue exclusion. T cells generated from HPCs were injectable with HIV-1 and produced up to 0.69 ng/ml of HIV-1 p24 by day 10 of culture. Both unsorted and sorted T cells generated form the co-cultures of HPCs on murine thymic stroma on Cellfoam and exposed to heat inactivated HIV$_{IIIB}$, produced undetectable levels of HIV-1 p24. The viability of T cells also declined significantly following exposure to infections HIV-1. The levels of HIV-1 p24 antigen production in T cells generated form the Cellfoam co-culture system was similar to levels of HIV-1 p24 production from human activated peripheral blood T cells.

Transduction of T cells Generated from HPC/Thymic Stromal Co-Cultures with an Amphotropic Murine Retroviral Vector:

T cells generated from HPCs and expanded in IL-2 and PHA were exposed to the murine retrovirus based vector, MFG, encoding the intranuclear localized enzyme β-galactosidase at an M.O.I. of 10 on three occasions over the period of 72 hours. Titred retroviral vector was generated by standard means from a human based FLYA4 packaging cell-line. T cells were also exposed to heat inactivated MFG. Transduced cells were harvested from cultures at 7 days following retroviral exposure and stained by standard methods for the expression of the beta-galactosidase transgene. Transduction efficiencies of between 12 and 26% were observed in T cells generated from co-cultures of HPCs with murine thymic stroma grown on Cellfoam. No β-galactosidase activity was detectable in T cells exposed to the heat inactivated retroviral vector. The transduction efficiency of human T cells generated from the Cellfoam co-culture system is similar to that seen in activated peripheral blood T cells.

mRNA Extraction and cDNA Synthesis:

Generated cells were also lysed and RNA was prepared from the cells for RNA PCR in order the determine T cell receptor gene expression. Messenger RNA was extracted from cells grown on a thymic monolayer. The extraction was performed using guanidinium thiocyanate and oligo-dT spun columns (QuickPrep® Micro mRNA Purification Kit; Pharmacia, Piscataway, N.J.) according to the manufacturer's instructions. mRNA samples were stored at −70° C. The first strand cDNA was synthesized in a 40 μl final volume, using approximately 2 μg of mRNA, 1 μg of random primer, and 6.25 units of AMV reverse transcriptase (GIBCO/BRL). Samples were incubated for 10 minutes at room temperature, 1 hour at 42° C., 5 minutes at 95° C., and 5 minutes at 4° C. RT-PCR for a number of lymphoid-specific genes (including RAG-2) was performed using reverse transcription using random primers and Moloney MuLV reverse transcriptase (GIBCO-BRL, Grand Island, N.Y.). cDNAs were amplified using gene-specific primers, e.g., for the human RAG-2 gene which is expressed transiently only by cells undergoing lymphocyte differentiation, Vβ gene expression, and the like. PCR amplification were performed in a GeneAmp® 9600 thermal cycler (Perkin Elmer, Norwalk, Conn.) using conditions well known in the art.

Example 1

Viability, Immunophenotype and Function of Human Cells Generated in Co-Culture Systems The numbers of viable cells generated in the co-culture system and their immunophenotype are shown in Table 5. Maximal human T cell proliferation was seen when human fetal thymic CD34+ cells and UCB CD34+ cells were co-cultured with murine fetal thymic stroma grown on Cellfoam. Data generated from a direct comparison of co-culture of CD34+ cells on murine thymic stroma on cell foam versus co-culture of CD34+ cells on murine stroma grown as a simple monolayer are also shown in Table 5.

T cells generated in the co-culture system were also shown to be injectable by T-tropic HIV-1$_{IIIB}$ and these cells were also transductible at a transduction efficiency of 12–22% (n=3) with MFG vector.

Example 2

Maintenance of Immature Progenitor Cells

According to the invention, it has also been discovered that Cellfoam cultures of thymic stromal cells are able to induce T cell differentiation of CD34+ progenitors and yet preserve a fraction of CD34+ cells. Primate CD34+ progenitors were cultured on either human or swine thymus that had been established on Cellfoam tissue scaffolds. After 14–21 days, CD3+CD4+CD8+ triple positive cells and CD3+CD4+ and CD3+CD8+ double positive cells are reliably recovered. In addition, the CD3− cell fraction was found to contain CD34+ progenitor cells after 14–21 days. These CD34+ cells not only were CD3−, but many were also CD2+. This demonstrates that thymus cultures in Cellfoam tissue scaffolds can support T cell differentiation while simultaneously preserving the long-lived CD34+ progenitor cell population. As will be evident to those skilled in the art, this surprising finding indicates that ongoing differentiation of T progeny while maintaining immature progenitor cells is possible in Cellfoam.

Example 3

T Cell Function (Proliferation/Anergy) Assays

T cell function is evaluated by the proliferative potential to specific and non-specific antigens using standard assays. Specifically, the assay assesses the response of T cell receptor (TCR) mediated proliferation using anti-CD3 antibodies (Becton Dickinson) as well as baseline non-specific proliferation using concavalin A (Con-A). Briefly, T cells are washed and resuspended in RPMI with 10% FCS at a concentration of $10^6$ cells/ml. 100 μl ($10^5$ cells) are added to each well of a 96 well plate. Cells are stimulated with either Con-A (5 μg/ml) (non-specific response) or monoclonal antibodies to CD3 in the presence of IL-2 (20 units/ml) and irradiated mononuclear cells (MCs) ($10^5$ cells/well in 100 ml of RPMI with 10% FCS). Purified goat anti-mouse F(ab')$_2$ fragments (Kirkegard and Perry Laboratories, Gaithersberg, Md.) are used as a crosslinking agent for the experimental conditions where monoclonal antibodies to CD3 are used. Wells are pretreated with 1.25 μg/ml of goat anti-mouse antibody for 45 minutes at 37° C. and washed three times prior to the addition of monoclonal antibodies to CD3 and CD28. Controls included T cells alone, T cells plus irradiated MCs, and T cells plus mitogenic stimuli without IL-2 or irradiated MC. After 7 days in culture at 37° C., cell proliferation are assessed using either radio-active assays or commercially available non-radioactive, ELISA based assays (e.g. Promega). Cells are co-cultured for 5–7 days to induce proliferation of the T cells (the stimulator cells are also irradiated and thus non-proliferative). Stimulator cells alone serve as controls.

An additional approach to testing T cell function uses flow cytometry based staining for intracellular expression of the cytokines IL-2 γIFN and TNFA using antibodies specific to the human forms of these factors (Becton Dickinson). These cytokines are produced in the T progeny in the antigen specific in vitro proliferation assays. This allows low level detection of human cells among a high proportion of mouse cells, selectively highlighting the human progeny and excluding the mouse cells. Further, semiquantitative RT-PCR of mRNA for these factors can also be used.

In one particular example, for instance, cells removed from co-culture after 14 days showed pronounced proliferation when placed in liquid culture with complete medium and IL-2 (10 IU/mL) and phytohemagglutinin (PHA; 2 µg/mL). After a further 7 days in culture there was a 45-fold increase in cell number: >90% were $CD3^+CD4^+TCR\alpha\beta^+$; 3% $CD3^+CD8^+TCR\alpha\beta^+$ and 3% $CD3^+CD8^+CD4^+TCR\alpha\beta^+$. No cells expressing $TCR\gamma\delta$ were detected.

selected population: this comprised only 0.57%±0.29% (mean±SEM; n=6) of the cells obtained from the selection process.

Example 5

Determination of Optium Matrix Size and Input Cell Number

Having tested matrices of differing dimensions we have determined that the optimal sized matrix for use in this system measures 10 mm diameter×1 mm in depth. Similarly, input cell density appears critical for optimum T-cell generation: no lymphocytes were generated using an input cell density of less than $1\times10^4$ cells per well. However, using 10×1 mm matrices and input cell densities of $1\times10^4$ or $1\times10^5$, we were able to generate large numbers of human cells, 71.21%±9.87% (mean SEM; n=7) of which were $CD3^+$, after 14 days in co-culture.

Example 6

Intra- and Inter-Sample Variability in Numbers of T-Cells Generated

TABLE 5

USE OF THYMIC STROMA/HUMAN FETAL CD34+CELL CO-CULTURE SYSTEM

| | Standard Protocol n = 3 Human UCB CD34+ Human fetal thymic stroma | | Fetal Human Thymic stroma n = 3 Cell foam Thy CD34+ | 6 Week Murine Thymic stroma n = 3 Cell foam Thy CD34+ | Neonatal swine Thymic stroma n = 3 Cel foam Thy CD34+ | Fetal Human Thymic stroma n = 3 Monolayer Thy CD34+ | 6 Week Murine Thymic stroma n = 3 monolayer Thy CD34+ | Neonatal Swine Thymic stroma n = 3 Monolayer Thy CD34+ |
|---|---|---|---|---|---|---|---|---|
| | d14 | d28 | d7 | d7 | d7 | d7 | d7 | d7 |
| CD4 | 2.8 | 3.8 | 81.54 | 85.8 | 67.8 | 88.2 | 81.1 | 69.2 |
| CD3 | 1.5 | 1.1 | 12.75 | 87.1 | 80.7 | 13.1 | 90.1 | 79.2 |
| CD4/CD3 | 4.2 | 1.4 | 9.83 | 75.2 | 64.65 | 10.6 | 68.1 | 66.3 |
| CD8/CD3 | 2.1 | 2.8 | 0.13 | 74.5 | 28.8 | 0.46 | 71.9 | 28.3 |
| CD4/CD8 | 1.8 | 1 | 0.37 | 79.5 | 25.4 | 0.89 | 89.1 | 22.9 |
| CD2 | 4.1 | 12.5 | ND | 23.2 | 50.7 | ND | 20.4 | 48.1 |
| CD14 | 33.4 | 16.1 | 59.6 | 0.17 | 6.8 | 63.1 | 0.81 | 4.6 |
| CD33 | 48.2 | 20.2 | 90.61 | 0.33 | ND | 84.1 | 0.59 | ND |
| CD2/CD14 | 1.6 | 7.3 | ND | 0.85 | ND | ND | 0.26 | ND |
| CD2/CD33 | 4.8 | 12.8 | ND | 3.76 | ND | ND | 4.12 | ND |
| CD33/CD14 | | 8.4 | 60.73 | 0.13 | ND | 56.13 | 0.11 | ND |
| Viable Cell Count $t_o$ = 5,000 | 195,000 | 210,000 | 98,000 | 1,800,000 | 220,000 | 15,000 | 79,000 | 51,000 |

Example 4

T Cell Lymphopoiesis Assay $AC133^+$ progenitor cells were added to the murine thymic stromal cultures at cell densities of either $1\times10^5$, $1\times10^4$, or $1\times10^3$ cells per well and cultured for an additional two weeks at 37° C. in a 5% $CO_2$ humidified atmosphere. Medium in the co-cultures was changed every 4 days and was not supplemented with exogenous cytokines. Cells generated from the precursors were harvested 7 and 14 days after establishment of the co-cultures.

The selected $AC133^+$ cells represented a highly purified progenitor cell population. Immunophenotypic analysis showed that >98% were $CD34^+$; none co-expressed surface CD3, CD4 or CD8. A small number of contaminating $CD2^+$ cells were detectable by flow cytometry within the AC133+

Figure 2:
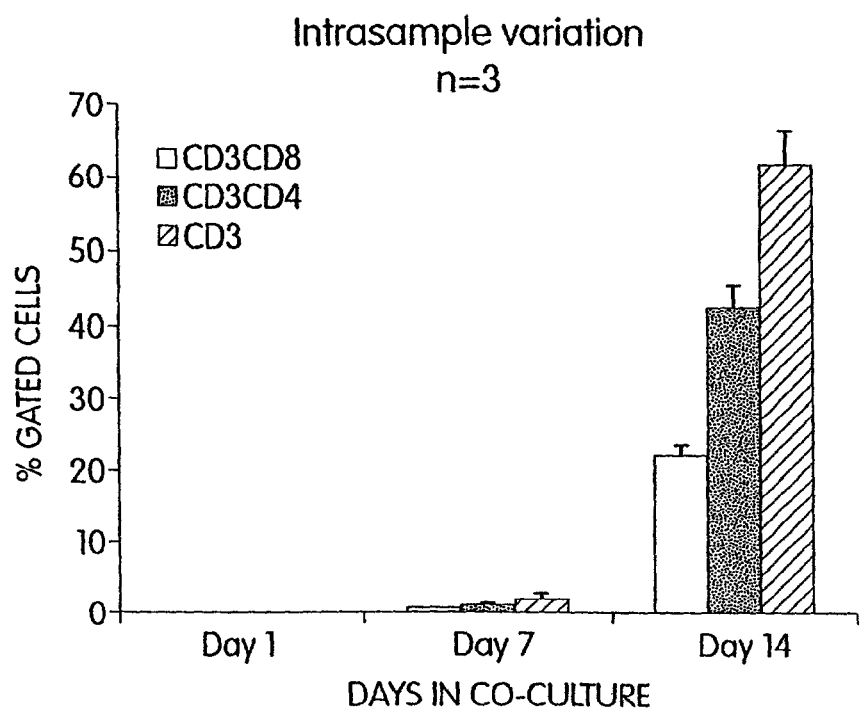
FIG. 2 shows the intrasample variability in numbers of T cells generated in a co-culture system of the invention.

In order to determine the variation of T-cell output within the a given source of progenitors, multiple co-cultures were established using a single source of AC133+ cells at fixed cell densities ($1\times10^4$ cells per well) on separate 10×1 mm matrices of murine thymic stroma. The intrasample variation of T lymphocytes generated was analyzed by cell count using trypan blue exclusion, and by immunophenotypic analysis. Human cells were distinguished by surface expression of CD45. After 7 days in co-culture, the number of mature T-cells detected was extremely low: $CD3^+$ cells represented 2.02%±0.87% (mean±standard error) of the $CD45^+$-gated population, $CD3^+CD4^+$ T-cells accounted for 1.0%±0.52% of the gated population and $CD3^+CD8^+$ 0.58%±0.1% of the same gated population. However, after 14 days, the numbers of T-cells were significantly higher: the proportion of $CD3^+$ cells rose to 62.16%±4.53%; and the percentages of $CD3^+CD4^+$ and $CD3^+CD8^+$ were 42.7%±2.87% and 22.39%±1.29% respectively. These data are represented graphically in FIG. 2.

Figure 3:
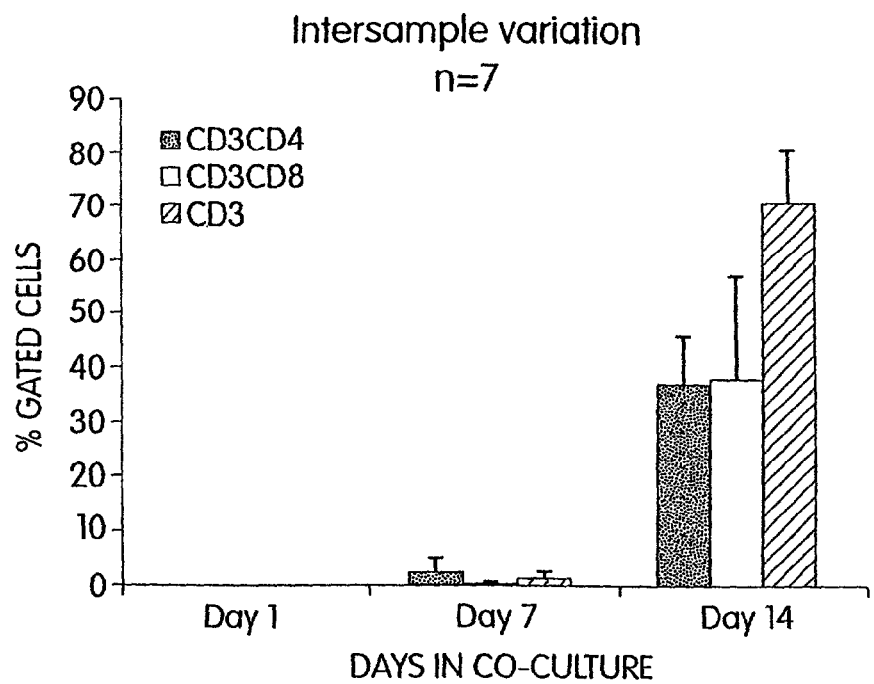
FIG. 3 shows the intersample variability in numbers of T cells generated in a co-culture system of the invention.

The intersample variation was calculated by comparing the number of T-cells generated from separate sources of CD34$^+$ progenitors. In each case a fixed number of cells ($1\times10^4$ cells per well) had been introduced into co-culture. Immunophenotypic analysis of cells generated after 7 days in co-culture showed that, of the CD45 gated population, 1.57%±0.97% of cells expressed CD3; 2.27%±2.70% co-expressed CD3 and CD4; and 0.46%±0.23% expressed both CD3 and CD8. After 14 days, the immunophenotype of the cells harvested revealed that 71.21%±9.87% were CD3$^+$; 37.44%±8.44% were CD3$^+$CD4$^+$, and 38.06%±19.13% were CD3$^+$CD8$^+$ as shown in FIG. 3.

These data demonstrate a high level of reproducibility within the system that suggests its potential in comparative analyses of input populations.

Example 7

Analysis for TCR Excision Circles (TREC)

The TCR Vδ locus lies between the TCR Vα and TCR Jα segments. In order to complete TCRα VD-J rearrangement, the TCR Vδ segment is excised: the 3' and 5' ends of the gene unite to form an extra-chromosomal circle of DNA termed a *TCR excision circle* (TREC) (Berenson R J, et al., *J Clin Invest*, 1988, 81: 951–5; Broxmeyer H E, et al, *Proc Natl Acad Sci USA*, 1989, 86:3828–32). TRECs do not duplicate when the T-cell divides (Blom B., et al., *J Immunol*, 1997, 158:3571–7). As a consequence, TREC levels are highest in recent thymic emigrants but are sequentially diluted amongst the emigrants' progeny. TCRδ TRECs are detectable by PCR—an assay that has been shown to be a reliable tool for monitoring de novo T-cell generation (Tjormford G E, et al., *J Exp Med*, 1993, 177:1531–9). Absolute numbers of TREC positive cells will vary according to the total number of cells analyzed. We determined that the significance of TREC positivity would be most fairly interpreted by calculating the ratio of the number of TREC copies detected to the number of β-actin copies detected. We compared the level of TREC detected in T-cells harvested from the co-cultures after 14 days to TREC levels in peripheral blood mononuclear cells, B cells, AC133$^+$ cells from the input population, and human fetal thymocytes. The highest TREC:bactin ratio was found in T-cells generated from the co-cultures after 14 days (0.54), followed by thymocytes from 16–22 week human fetuses (0.017). The TREC:bactin ratios from fetal and adult PBMCs and from AC133$^+$ bone marrow mononuclear cells was significantly lower. These data are summarized in Table 6, below. No TREC was detected in any of the samples of B-cells tested (n=6).

TABLE 6

| Source | n | TREC/Bactin ratio (mean) |
|---|---|---|
| Murine Thymocytes | 6 | 0 |
| Bone Marrow AC133+ progenitors | 3 | 0.000014 |
| Adult Peripheral blood MNCs | 3 | 0.00141 |
| Fetal Peripheral blood MNCs | 1 | 0.0024 |
| Fetal Thymocytes | 2 | 0.017 |
| T-Cells generated in vitro | 2 | 0.54 |

These data conclusively demonstrate that rearrangement of TCR occurs during the course of the culture period. The abundance of TREC positive cells compares favorably with that seen from fresh fetal thymus and supports the physiologic equivalence of the in vitro system in this aspect of T-cell differentiation.

Those skilled in the art will recognize, or be able to ascertain using no more than o routine experimentation, many equivalents to the specific embodiments of the invention described herein. Such equivalents are intended to be encompassed by the following claims.

All references disclosed herein are incorporated by reference in their entirety. What is claimed is presented below, followed by a Sequence Listing.

We claim:

1. A method for in vitro production of lymphoid tissue-specific cells, comprising:
   introducing an amount of hematopoietic progenitor cells, an amount of antigen presenting cells, and an amount of lymphoreticular stromal cells, into a porous, solid matrix having interconnected pores of a pore size sufficient to permit the hematopoietic progenitor cells, the antigen presenting cells, and the lymphoreticular stromal cells to grow throughout the matrix,
   wherein the lymphoreticular stromal cells are derived from at least one lymphoid soft tissue selected from the group consisting of spleen, liver, lymph node, skin, tonsil and Peyer's patches, and combinations thereof, and the amount of the lymphoreticular stromal cells is sufficient to support the growth and differentiation of the hematopoietic progenitor cells, and
   co-culturing the hematopoietic progenitor cells, antigen presenting cells, and lymphoreticular stromal cells and thereby producing the lymphoid tissue-specific cells,
   wherein the lymphoid tissue-specific cells are T-cells.

2. The method of claim 1, wherein the co-culturing occurs under conditions sufficient to produce at least a 10-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

3. The method of claim 1, wherein the co-culturing occurs under conditions sufficient to produce at least a 20-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

4. The method of claim 1, wherein the co-culturing occurs under conditions sufficient to produce at least a 50-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

5. The method of claim 1, wherein the co-culturing occurs under conditions sufficient to produce at least a 100-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

6. The method of claim 1, wherein the co-culturing occurs under conditions sufficient to produce at least a 200-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

7. The method of claim 1, wherein the co-culturing occurs under conditions sufficient to produce at least a 400-fold increase in the number of lymphoid tissue-specific cells when compared to the number of lymphoid tissue-specific cells produced in a control co-culture of hematopoietic progenitor cells, antigen presenting cells, and lymphoreticular stromal cells grown in a monolayer.

8. The method of claim 1, wherein the hematopoietic progenitor cells are selected from the group consisting of pluripotent stem cells, multipotent progenitor cells and progenitor cells committed to specific hematopoietic lineages.

9. The method of claim 8, wherein the progenitor cells committed to specific hematopoietic lineages are committed to a T cell lineage.

10. The method of claim 9, wherein the lymphoreticular stromal cells are skin stromal cells.

11. The method of claim 1, wherein the hematopoietic progenitor cells are derived from tissue selected from the group consisting of bone marrow, peripheral blood, umbilical cord blood, placental blood, lymphoid soft tissue, fetal liver, embryonic cells and aortal-gonadal-mesonephros derived cells.

12. The method of claim 8, wherein the lymphoid soft tissue is selected from the group consisting of thymus, spleen, liver, lymph node, skin, tonsil and Peyer's patches.

13. The method of claim 1, wherein the hematopoietic progenitor cells and the lymphoreticular stromal cells are autologous.

14. The method of claim 1, wherein the hematopoietic progenitor cells and the lymphoreticular stromal cells are non-autologous.

15. The method of claim 1, wherein the hematopoietic progenitor cells, antigen presenting cells, and the lymphoreticular stromal cells are autologous.

16. The method of claim 13, wherein the hematopoietic progenitor cells and the lymphoreticular stromal cells are non-autologous to the antigen presenting cells.

17. The method of claim 1, wherein the hematopoietic progenitor cells and the antigen presenting cells are autologous.

18. The method of claim 1, wherein the hematopoietic progenitor cells and the antigen presenting cells are non-autologous.

19. The method of claim 18, wherein the lymphoreticular stromal cells and the antigen presenting cells are non-autologous.

20. The method of claim 19, wherein the hematopoietic progenitor cells and the lymphoreticular stromal cells are non-autologous.

21. The method of claim 18, wherein the lymphoreticular stromal cells and the antigen presenting cells are autologous.

22. The method according to any of claims 1 or 8–21, further comprising adding at least one antigen to the lymphoid tissue-specific cells.

23. The method of claim 1, wherein the antigen presenting cells are mature.

24. The method of claim 1, wherein the lymphoid tissue-specific cells are to be used in transplantation into a host and wherein the hematopoietic progenitor cells are non-autologous to the cells of the host.

25. The method of claim 1, wherein the lymphoid tissue-specific cells are to be used in transplantation into a host and wherein the hematopoietic progenitor cells are autologous to the cells of the host.

26. The method of claim 1, wherein the lymphoid tissue-specific cells are to be used in transplantation into a host and wherein the lymphoreticular stromal cells are non-autologous to the cells of the host.

27. The method of claim 1, wherein the lymphoid tissue-specific cells are to be used in transplantation into a host and wherein the lymphoreticular stromal cells are autologous to the cells of the host.

28. The method according to one of claims 23–27, further comprising adding at least one antigen to the lymphoid tissue-specific cells.

29. The method according to any of claims 1 or 23–27, wherein the lymphoid tissue-specific cells are to be used in transplantation into a host and wherein the antigen presenting cells are non-autologous to the cells of the host.

30. The method according to any of claims 1 or 23–27, wherein the lymphoid tissue-specific cells are to be used in transplantation into a host and wherein the antigen presenting cells are autologous to the cells of the host.

31. The method of claim 29, further comprising adding at least one antigen to the lymphoid tissue-specific cells.

32. The method of claim 30, further comprising adding at least one antigen to the lymphoid tissue-specific cells.

33. The method according to any of claims 1 or 8–21, wherein the hematopoietic progenitor cells are genetically altered hematopoietic progenitor cells.

34. The method of claim 33, further comprising adding at least one antigen to the lymphoid tissue-specific cells.

35. The method of claim 1, wherein the lymphoreticular stromal cells are genetically altered lymphoreticular stromal cells.

36. The method of claim 1, wherein the lymphoreticular stromal cells are seeded prior to inoculating the hematopoietic progenitor cells.

37. The method of claim 1, wherein the lymphoreticular stromal cells are seeded at the same time as the hematopoietic progenitor cells.

38. The method of claim 1, wherein the hematopoietic progenitor cells are of human origin and the lymphoreticular stromal cells are of human origin.

39. The method of claim 1, wherein the hematopoietic progenitor cells are of human origin, the lymphoreticular stromal cells are of human origin, and the antigen presenting cells are of human origin.

40. The method of claims 1, wherein the hematopoietic progenitor cells are of human origin and the lymphoreticular stromal cells are of nonhuman origin.

41. The method of claim 40, wherein the nonhuman origin lymphoreticular stromal cells are of murine origin.

42. The method of claim 1, wherein the hematopoietic progenitor cells, the lymphoreticular stromal cells, and the antigen presenting cells are cultured in an environment that is free of stromal cell conditioned medium and exogenously added hematopoietic growth factors that promote hematopoietic cell maintenance, expansion, and differentiation, other than serum.

43. The method of claim 42, wherein the hematopoietic growth factors that promote hematopoietic cell maintenance, expansion, and differentiation, are agents selected from the group consisting of interleukins 3, 6 and 11.

44. The method of claim 42, further comprising adding at least one antigen to the lymphoid tissue-specific cells.

45. The method of claim 1, wherein the hematopoietic progenitor cells, the lymphoreticular stromal cells, and the antigen presenting cells are cultured with an exogenously added agent selected from the group consisting of stromal cell conditioned medium, and a hematopoietic growth factor that promotes hematopoietic cell maintenance, expansion, differentiation, and influences cell localization.

46. The method of claim 45, wherein the hematopoietic growth factor that promotes hematopoietic cell maintenance, expansion, differentiation, and influences cell localization, is an agent selected from the group consisting of interleukin 3, interleukin 6, interleukin 7, interleukin 11, interleukin 12, stem cell factor, FLK-2 ligand, FLT-2 ligand, Epo, Tpo, GMCSF, GCSF, Oncostatin M, and MCSF.

47. The method of claim 45, further comprising adding at least one antigen to the lymphoid tissue-specific cells.

48. The method of claim 1, further comprising: after the co-culturing step, harvesting the lymphoid tissue-specific cells.

49. The method of claim 48, further comprising adding at least one antigen to the lymphoid tissue-specific cells.

50. The method of claim 1, further comprising adding at least one antigen to the co-cultured cells.

51. The method of claim 50, wherein the at least one antigen is added during the co-culture of the cells.

52. The method of claim 50, wherein the at least one antigen is added after the co-culture of the cells.

53. The method of claim 50, wherein the at least one antigen is added to the co-cultured cells after formation of the lymphoid tissue-specific cells.

* * * * *